(12) United States Patent
de Fonseca et al.

(10) Patent No.: US 8,188,312 B2
(45) Date of Patent: May 29, 2012

(54) ACYCLIC SULFAMIDE DERIVATIVES

(75) Inventors: Fernando Antonio Rodriguez de Fonseca, Málaga (ES); Manuel Macias Gonzalez, Málaga (ES); Javier Pavon Moron, Málaga (ES); María Pilar Goya-Laza, Madrid (ES); Juan Antonio Paez Prosper, Madrid (ES); Carolina Cano Ramos, Madrid (ES)

(73) Assignees: Fundacion Imabis. Instituto Mediterraneo para el Avance de la Biotecnologia y la Investigacion Sanitaria (ES); Consejo Superior de Investigaciones Cientificas (ES)

( * ) Notice: Subject to any disclaimer, the term of this patent is extended or adjusted under 35 U.S.C. 154(b) by 513 days.

(21) Appl. No.: 12/162,035

(22) PCT Filed: Jan. 26, 2007

(86) PCT No.: PCT/EP2007/000681
§ 371 (c)(1),
(2), (4) Date: Jan. 12, 2009

(87) PCT Pub. No.: WO2007/085469
PCT Pub. Date: Aug. 2, 2007

(65) Prior Publication Data
US 2009/0221710 A1  Sep. 3, 2009
US 2010/0048712 A2  Feb. 25, 2010
US 2010/0179224 A2  Jul. 15, 2010

(30) Foreign Application Priority Data

Jan. 27, 2006  (ES) .................................. 200600184

(51) Int. Cl.
C07C 307/06  (2006.01)
A61K 31/18  (2006.01)

(52) U.S. Cl. .......................................... 564/79; 514/600
(58) Field of Classification Search .................... 564/79
See application file for complete search history.

(56) References Cited

U.S. PATENT DOCUMENTS

| 3,772,207 A | 11/1973 | Michalski et al. |
| 4,171,223 A | 10/1979 | Odenwalder et al. |
| 4,218,357 A | 8/1980 | Mark et al. |
| 4,252,951 A * | 2/1981 | Jackson et al. ............. 540/220 |
| 2005/0054730 A1 | 3/2005 | Fu |

OTHER PUBLICATIONS

Braga et al., Chem. Commun. (2005), 29, p. 3635-3645.*
Cano et al., "Novel Sulfamide Analogs of Oleoylethanolamide Showing In Vivo Satiety Inducing Actions and PPAR-α Activation," J. Med. Chem., vol. 50, pp. 389-393, 2007, published on web Dec. 20, 2006.
Fu et al., "Oleoylethanolamide, an Endogenous PPAR-α Agonist, Lowers Body Weight and Hyperlipodemia in Obese Rats," Neuropharmacology, vol. 48, pp. 1147-1153, Apr. 21, 2005.
Fu et al., "Oleoylethanolamide Regulates Feeding and Body Weight Through Activation of the Nuclear Receptor PPAR-α," Nature, vol. 425, pp. 90-93, Sep. 4, 2003.
Rodriguez et al., "An Anorexic Lipid Mediator Regulated by Feeding," Nature, vol. 414, pp. 209-212, Nov. 8, 2001.

* cited by examiner

*Primary Examiner* — Brian J Davis
(74) *Attorney, Agent, or Firm* — Kenneth H. Sonnenfeld; King & Spalding

(57) ABSTRACT

The present invention is related to acyclic sulfamide derivatives, useful for the manufacture of a medicament for satiety induction and ingestion control, corporal fat modulation and lipidic metabolism regulation and for the manufacture of a medicament for the treatment or prevention of diabetes and cardiovascular diseases. The acyclic sulfamide derivatives are also useful for cosmetic use.

23 Claims, 7 Drawing Sheets

ACYCLIC SULFAMIDE DERIVATIVES

FIELD OF THE INVENTION

The present invention is related to acyclic sulfamide derivatives, useful for the treatment of obesity and feeding disorders.

BACKGROUND OF THE INVENTION

There is an increasing need for the provision of active compounds for the treatment of obesity and feeding disorders. In recent years there has been a substantial research effort in finding new pharmacological targets for the treatment of these conditions.

One of the most promising targets discovered are peroxisome proliferator activated receptors (PPAR) which are a superfamily belonging to the nuclear hormone receptors, which are ligand activated transcription factors that play a key role in the regulation of the metabolism of lipids and carbohydrates. In addition, it has been discovered that PPAR's also play a key role in satiety induction and ingestion control and corporal fat modulation, as well as in the treatment and prevention of diabetes and cardiovascular diseases.

Three subtypes of PPAR receptors have been described: PPARalpha, PPARgamma and PPARdelta (Kota, B. P. et al. *Pharmacol. Res.* 51 (2005): 85). The activation by ligands of the PPARgamma subtype enhances the actions of insulin in man and reduces the levels of circulating glucose in diabetes models of rodents. The PPARgamma receptor expressed in adipose tissue, plays a key function in the regulation of the adipocyte differentiation in vitro. The biology of the PPARdelta subtype is less known, although it seems to play an important role in the control of the hyperglycemia and the hyperlipidaemia (Berger, J. y Moller, D. E. *Annu. Rev. Med.* 53 (2002): 409; Berger, J. et al. *J. Biol. Chem.* 274 (1999): 6718-6725).

The activation of PPARalpha subtype by its natural ligands is related to the control of the levels of circulating lipids. Fatty acids of medium and long chain and eicosanoids (Forman, B. M. et al. *Proc. Natl. Acad. Sci. U.S.A.* 94 (1997): 4312) have been described, which produce a substantial reduction of the plasma triglycerides, a moderate reduction of the cholesterol associated with low density lipoproteins (LDL) and a satiety effect. Hence, the alpha subtype of this receptor family is presented as a very interesting therapeutical target for the treatment of diseases related to metabolic alterations, such as dyslipidemias, cardiovascular illness, diabetes and obesity (Cheng, P. T. et al. *Mini. Rev. Med. Chem.* 5 (2005): 741; Evans, R. M. et al. *Nature Medicine* 10 (2004): 361).

The dyslipidemias are disorders in the lipids metabolism characterized by abnormal concentrations of one or more types of lipids (e.g. cholesterol and triglycerides), and/or apolipoproteins (e.g. type A, B, C and E), and/or lipoproteins (e.g. low density lipoproteins (LDL), very low density lipoproteins (VLDL) and intermediate density lipoproteins (IDL)). The cholesterol molecule is normally transported bound to LDL lipoproteins. The increase of the levels of this composition is directly related to the risk of coronary disease. A smaller percentage of the cholesterol molecule is transported trough the HDL lipoproteins, whose main function is extracting the cholesterol deposited on the arterial walls and transport it to the liver for being eliminated trough the intestine. It has been described that a high level of HDL-cholesterol is associated with the decrease of the risk of coronary disease. Therefore, in the treating of dyslipidemias, decreasing the LDL-cholesterol levels is as important as increasing the HDL-cholesterol levels (Gordon, T. et al. *Am. J. Med.* 62 (1977): 707. Stampfer; M. J. et al. *N. England J. Med.*, 325 (1991): 373; Kannel, W. B. et al. *Ann. Internal Med.* 90 (1979): 85-91). At present, fibrate derivatives, such as clofibrate (WO 02009682), bezafibrate and phenofibrate (WO 02015845) are being clinically used for the control of dyslipidemias by binding to the PPARalpha subtype, thus controlling some transcription factors implicated in some of the processes previously described (Linton, M. F. y Fazio, M. F. *Curr. Atherioscler. Rep.* 2 (2000): 29).

As well as for the treatment of dyslipidemias, dual agonist agents of PPARalpha/gamma are utilized with a potential use for the treatment of diabetes type 2 (Henke, B. R. *J. Med. Chem.* 47 (2004): 4118). Different glitazones (benzyl-2,4-thiazolidindione derivatives) have been approved for their use in the treatment of diabetes. Among them isaglitazon (WO 03018010), troglitazon, rosiglitazon and pioglitazon (Hulin, B. et al. *Current Pharm. Design.* 2 (1996): 85) are included. New molecules in development or in different phases of clinical research are demonstrating a dual activity as activators of the PPARalpha and gamma subtypes, such as KRP-297 (Murakami, K. *Biochem. J.* 353 (2001): 231), some thiazoles (WO 01021602) and propionic acid derivatives (WO 02069994).

Finally, different research lines are focusing on the development of selective agents of the PPARalpha subtype, such as phenylpropionic acid derivatives (Nombra, M. et al. *J. Med. Chem.* 46 (2003): 3581) or those of triazole and triazolone LY518674 (Xu, Y. et al. *J. Med. Chem.* 46 (2003): 5121) as potential treatment of diseases related to disorders of the lipidic profile and corporal fat composition.

US 2004/0176426 describes compounds having the following formula

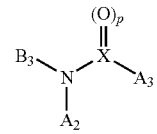

wherein $A_2$ and $A_3$ can be alkyl, heteroalkyl, cycloalkyl, heterocycloalkyl, cycloalkenyl, heterocycloalkenyl, aryl, heteroaryl, arylalkyl, (heteroaryl)alkyl, aryl(heteroalkyl), or (heteroaryl)heteroalkyl; $B_3$ is selected from -hydrogen, -alkylene-C(O)$R_3$, —C(O)$R_3$, alkylene-C(O)N($R_3R_4$), —C(O)N($R_3R_4$), alkylene-S(O)$_n$N($R_3R_4$), S(O)$_n$N($R_3R_4$) alkylene-N($R_3R_4$), alkylene-OR$_3$, and —C(O)OR$_3$ (wherein $R_3$ and $R_4$ can be hydrogen, alkyl, heteroalkyl, cycloalkyl among others); X is C, S, or N; and p is an integer from 0 to 2.

The compounds described in US 2004/0176426 are useful in modulating the farnesoid X receptor (FXR). According to US 2004/0176426 FXR forms heterodimers with the retinoid X receptor (RXR) in some cell types, modulation of the level of FXR activity in cells has a wide range of effects on a variety of biological processes which are mediated by RXR or other RXR-interacting proteins such as PPARgamma and PPARalpha.

However, from all the possible families of compounds described in US 2004/0176426, no mention is made to acyclic sulfamide derivatives or to their activity in satiety induction and ingestion control, corporal fat modulation and lipidic metabolism regulation or for the treatment or prevention of diabetes and cardiovascular diseases.

U.S. Pat. No. 4,171,223 describes non-diffusible thioether compounds capable of reacting with the oxidation products of a primary aromatic amino colour developer substance to release a diffusible silver halide development inhibitor compound with the following formula

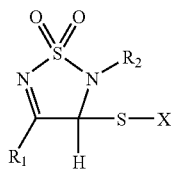

N-dodecyl-sulfamide is disclosed in the same document as an intermediate for the synthesis of the above compounds.

U.S. Pat. No. 4,218,357 describes compounds with the following formula

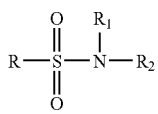

wherein R is selected from the group consisting of $C_1$ to $C_{30}$ alkyl, cycloalkyl of 4 to 10 carbon atoms, aryl of 6 to 14 carbon atoms and substituted aryl or $C_1$ to $C_{30}$ alkoxy, among others; and $R_1$ and $R_2$ are independently selected from hydrogen and the group consisting of $C_1$ to $C_{30}$ alkyl, cycloalkyl of 4 to 10 carbon atoms, aryl of 6 to 14 carbon atoms and substituted aryl.

The compounds described in U.S. Pat. No. 4,218,357 are platifiers used as additives for polymers. Specifically, U.S. Pat. No. 4,218,357 discloses the following compound

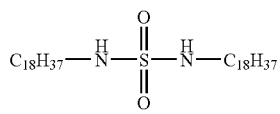

as a suitable plastifier additive.

Although the current agents are giving good results in the treatment of some of the above mentioned diseases, it is still necessary to continue searching alternative compounds with therapeutic potential, better pharmacokinetic properties and reduced toxicity.

SUMMARY OF THE INVENTION

Figure 1:
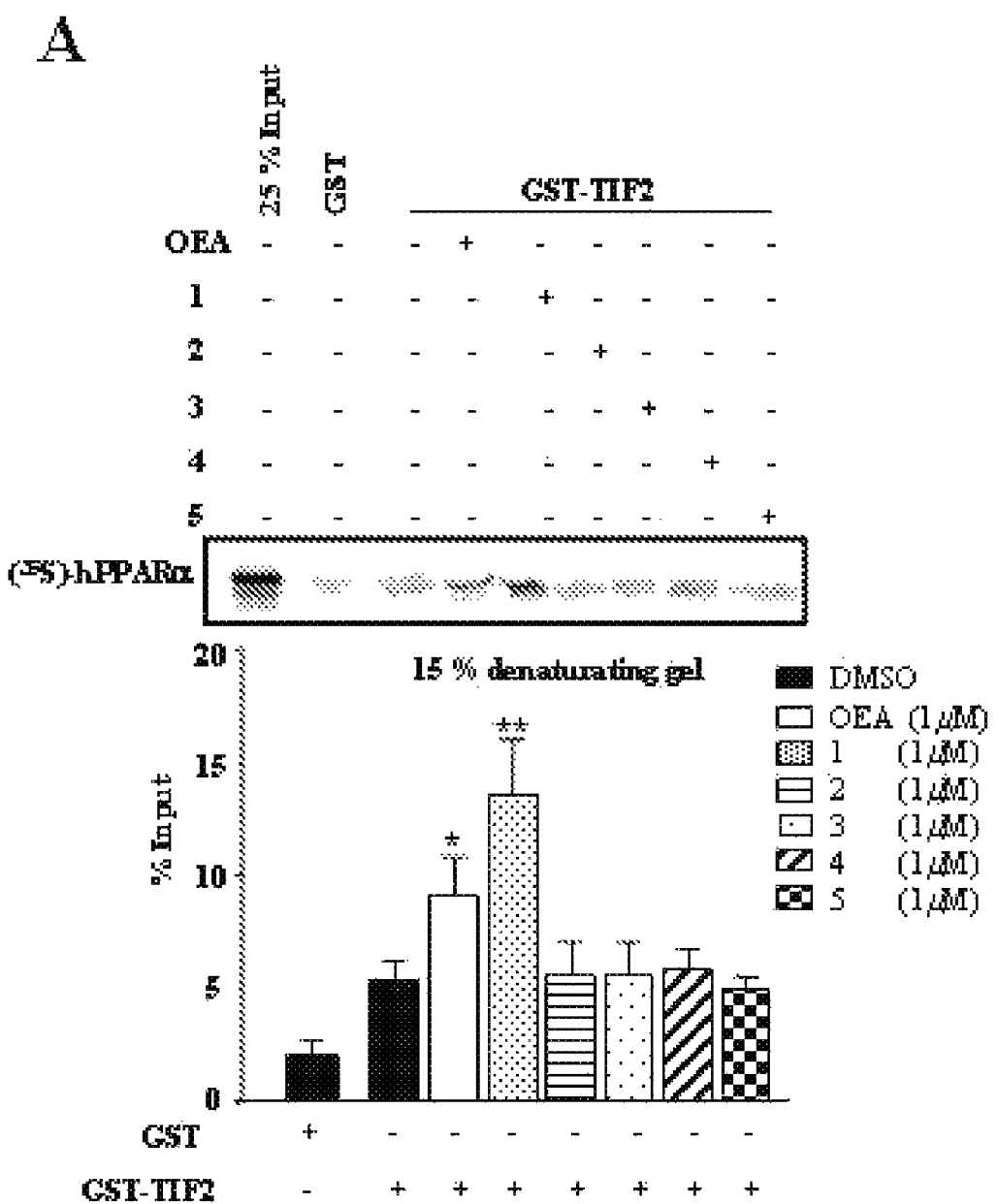
FIG. 1: Individual ligand-triggered interaction profiles of hPPARα with coactivator (CoA) in solution. GST pull down assays were performed with bacterially expressed coactivator GST-CoA and full-length in vitro translated ($^{35}$S)-labeled human PPARα, in absence and presence of their respective ligands. GST alone (−) was used as a control. After precipitation and washing the samples were electrophoresed through 15% SDS-PAGE gels and the percentage of precipitated NR in respect to input was quantified using a Fuji FLA3000 reader. Representative gels are shown. Columns represent the mean values of at least three experiments and the bars indicate standard deviations (SD). Statistical analysis was performed using a two tail, paired Student's t-test and p values were calculated in reference to vehicle (*p<0.05 and **p<0.01). (A) Compounds 1-5; (B) Compounds 6-9; (C) Compounds 10-12.
Figure 1:
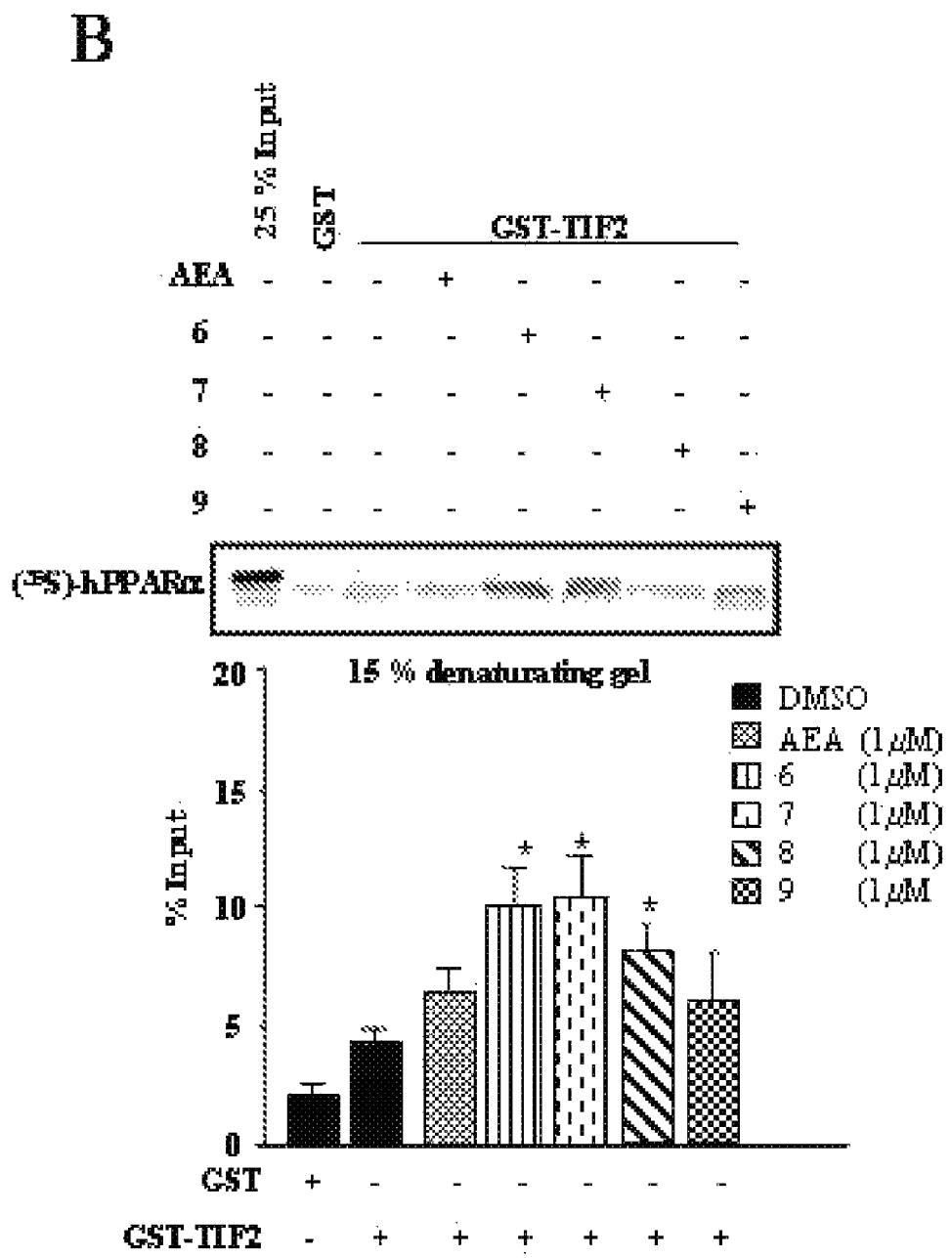
Figure 1:
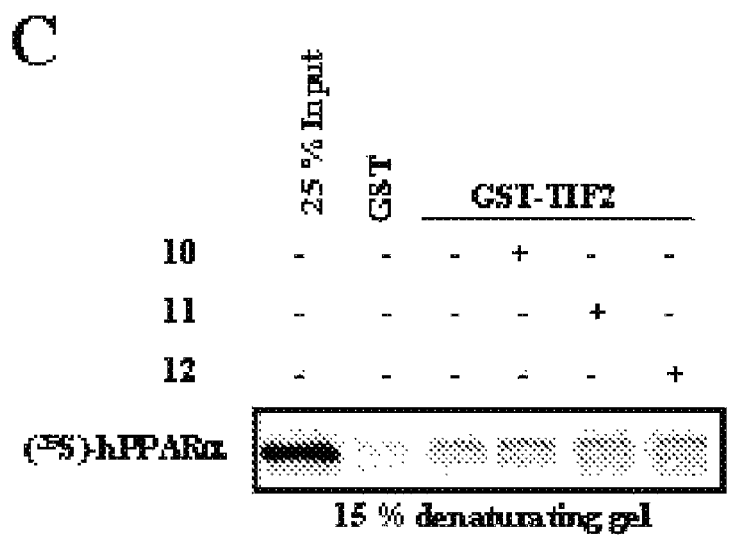
Figure 1:
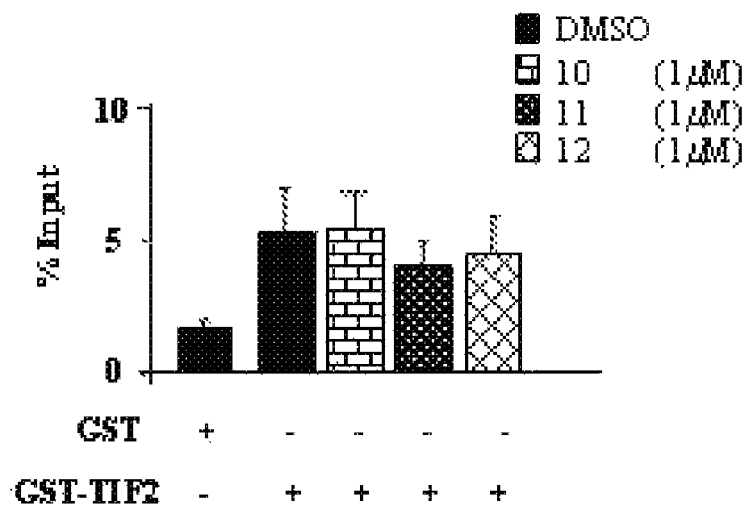

The inventors have found a new class of molecules which, surprisingly, are capable of inducing satiety and control ingestion, modulate corporal fat and regulate lipidic metabolism and useful for the manufacture of a medicament for the treatment or prevention of diabetes and cardiovascular diseases.

Thus, according to a first aspect, the present invention is directed to acyclic sulfamide derivatives of formula (I),

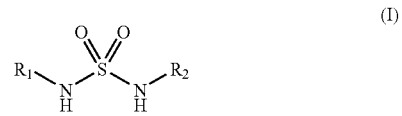

wherein $R_1$ and $R_2$ may be the same or different,
when $R_1$ and $R_2$ are different,
$R_1$ is selected from the group consisting of linear $C_{12}$-$C_{20}$ alkyl and linear $C_{12}$-$C_{20}$ alkenyl comprising 1, 2, 3 or 4 double bonds; and R$_2$ is selected from the group consisting of hydrogen and C$_1$-C$_4$ alkyl;
or
when R$_1$ and R$_2$ are the same,
R$_1$ and R$_2$ are selected from the group consisting of linear C$_{14}$-C$_{20}$ alkyl and linear C$_{14}$-C$_{20}$ alkenyl with 1, 2, 3 or 4 double bonds;
with the proviso that
when R$_1$ is n-dodecyl, then R$_2$ is not hydrogen; and
when R$_1$ and R$_2$ are the same, then they are not C$_{1-8}$ alkyl groups;
and pharmaceutically acceptable salts, solvates and hydrates thereof.

According to a second aspect, the present invention is directed to said compounds of formula (I) for use as a medicament.

According to a third aspect, the present invention is directed to the use of said compounds of formula (I) for the manufacture of a medicament for satiety induction and ingestion control, corporal fat modulation and lipidic metabolism regulation and for the treatment or prevention of diabetes and cardiovascular diseases or a method for satiety induction and ingestion control, corporal fat modulation and lipidic metabolism regulation and for the treatment or prevention of diabetes and cardiovascular diseases comprising administering to a patient in need of such treatment a therapeutically effective amount of a compound of formula (I).

According to a fourth aspect, the present invention is directed to a pharmaceutical composition comprising a compound of formula (I) and one or more pharmaceutically acceptable excipients.

According to a fifth aspect, the present invention is directed to the cosmetic use of a compound of formula (I) for reducing subcutaneous fat.

DESCRIPTION OF THE INVENTION

Compounds of Formula I

As mentioned above, a first aspect of the present invention is directed to acyclic sulfamide derivatives of formula (I),

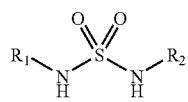
(I)

wherein R$_1$ and R$_2$ may be the same or different,
when R$_1$ and R$_2$ are different,
R$_1$ is selected from the group consisting of linear C$_{12}$-C$_{20}$ alkyl and linear C$_{12}$-C$_{20}$ alkenyl comprising 1, 2, 3 or 4 double bonds; and
R$_2$ is selected from the group consisting of hydrogen and C$_1$-C$_4$ alkyl;
or
when R$_1$ and R$_2$ are the same,
R$_1$ and R$_2$ are selected from the group consisting of linear C$_{14}$-C$_{20}$ alkyl and linear C$_{14}$-C$_{20}$ alkenyl with 1, 2, 3 or 4 double bonds;
with the proviso that
when R$_1$ is n-dodecyl, then R$_2$ is not hydrogen; and
when R$_1$ and R$_2$ are the same, then they are not C$_{1-8}$ alkyl groups;
and pharmaceutically acceptable salts, solvates and hydrates thereof.

"Alkyl" refers to a hydrocarbon chain radical consisting of carbon and hydrogen atoms, containing no unsaturation, which is attached to the rest of the molecule by a single bond.

The term "alkenyl" means a hydrocarbon chain radical having one, two, three or four carbon-carbon double bonds therein and which is attached to the rest of the molecule by a single bond. The double bond of an alkenyl group can be unconjugated or conjugated to another unsaturated group.

"C$_{12}$-C$_{20}$" indicates that the radical which follows comprises 12 to 20 carbon atoms (i.e., 12, 13, 14, 15, 16, 17, 18, 19 or 20 carbon atoms). Analogously, "C$_{14}$-C$_{20}$" indicates that the radical comprises 14 to 20 carbon atoms (i.e., 14, 15, 16, 17, 18, 19 or 20 carbon atoms), "C$_{16}$-C$_{20}$" indicates that the radical comprises 16 to 20 carbon atoms (i.e., 16, 17, 18, 19 or 20 carbon atoms), "C$_1$-C$_4$" indicates that the radical comprises 1 to 4 carbon atoms (i.e., 1, 2, 3 or 4 carbon atoms), and "C$_x$" indicates that the radical comprises "x" carbon atoms.

It is evident for the skilled person that many variations and configurations are possible and can be obtained at will depending on the compounds selected as starting materials, the relative configurations of the functional groups present, the presence or not of chiral centers, and on the combination of reactions that are applied. The present invention encompasses all such variations (enantiomers, diastereoisomers or tautomers) and possibilities.

The invention also provides salts of compounds of formula (I) with biologically and pharmacologically acceptable inorganic and organic acids, non-limiting examples of which are sulphates; hydrohalide salts; phosphates; lower alkane sulphonates; arylsulphonates; salts of C$_1$-C$_{20}$ aliphatic mono-, di- or tribasic acids which may contain one or more double bonds, an aryl nucleus or other functional groups such as hydroxy, amino, or keto; salts of aromatic acids in which the aromatic nuclei may or may not be substituted with groups such as hydroxyl, lower alkoxyl, amino, mono- or di-lower alkylamino sulphonamido. Also included within the scope of the invention are quaternary salts of the tertiary nitrogen atom with lower alkyl halides or sulphates, and oxygenated derivatives of the tertiary nitrogen atom, such as the N-oxides. In preparing dosage formulations, those skilled in the art will select the pharmaceutically acceptable salts.

The term "pharmaceutically acceptable salts" refers to any salt, which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, can be carried out by methods known in the art.

For instance, pharmaceutically acceptable salts of compounds provided herein may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkylenethanolamine, triethanolamine, glucamine and basic aminoacids salts. Examples of the metallic salts include, for example, sodium, potassium, calcium, magnesium, aluminium and lithium salts.

The invention also provides solvates of the compounds of formula (I). The term "solvate" according to this invention is to be understood as meaning any form of the compounds of formula (I) according to the invention which has another molecule (most likely a polar solvent) attached to it via non-covalent bonding. Examples of solvates include hydrates and alcoholates, e.g. methanolate.

According to a preferred embodiment, $R_2$ is a $C_1$-$C_4$ alkyl when $R_1$ and $R_2$ are different.

According to a preferred embodiment, $R_2$ is propyl, when $R_1$ and $R_2$ are different.

According to a preferred embodiment, $R_2$ is hydrogen, when $R_1$ and $R_2$ are different.

According to another preferred embodiment, $R_1$ is a linear $C_{16}$-$C_{20}$ alkyl or a linear $C_{16}$-$C_{20}$ alkenyl comprising 1, 2, 3 or 4 double bonds, when $R_1$ and $R_2$ are different.

According to another preferred embodiment, the alkenyl group of $R_1$ has 1 double bond when $R_1$ and $R_2$ are different.

According to another preferred embodiment, the compound of formula (I) is selected from one of the following:
N-(cis-9-octadecenyl)sulfamide;
N-octadecylsulfamide;
N-hexadecylsulfamide;
N-tetradecylsulfamide;
N-(cis-9-octadecenyl)-N'-propylsulfamide;
N-octadecyl-N'-propylsulfamide;
N-hexadecyl-N'-propylsulfamide;
N-propyl-N'-tetradecylsulfamide;
N,N'-bis(9-cis-octadecenyl)sulfamide;
N-(cis-9-cis-12-octadecadienyl)sulfamide;
N-(cis-5-cis-8-cis-11-cis-14-eicosatetraenyl)sulfamide;
N-(cis-5-cis-8-cis-11-cis-14-eicosatetraenyl)-N'-propylsulfamide;
N-(cis-5-cis-8-cis-11-cis-14-octadecadienyl)N'-propylsulfamide;
N-(trans-9-octadecenyl)sulfamide; and
N-(trans-9-octadecenyl)-N'-propylsulfamide;
and pharmaceutically acceptable salts, solvates and hydrates thereof.

Synthesis of the Compounds of Formula (I)

The preparation of the compounds of formula (I) can be performed according to the reaction sequence described in scheme 1.

The synthetic route described in scheme 1 consists of the reaction of the sulfamide of formula (II) with the corresponding monosubstituted amines of formula (III), according to described procedures (Mc Dermott, S. D. y Spillane, W. *J. Org. Prep. Proc. Int.* 16 (1984): 49), although the reaction conditions were modified to provide the compounds of formula (I).

Derivatives of N-alkylsulfamoyl of formula (IV), wherein $R_1$ has the meaning previously mentioned, were prepared following the reaction procedure of Atkins and Burgess (Atkins, G. M. Jr.; Burgess, E. M. *J. Am. Chem. Soc.* 94 (1972): 6135) from the corresponding amines of formula (III) with a N-alkylsulfamoyl of formula (IV) prepared in situ according to the procedure described by Kloek and Leschinsky (Kloek, J. A.; Leschinsky, K. L. *J. Org. Chem.* 41 (1976): 4028).

Scheme 1

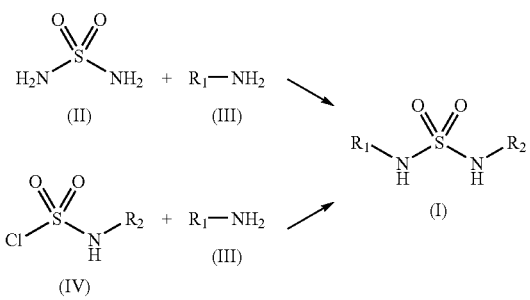

Use of the Compounds of Formula (I)

According to a second aspect, the present invention is directed to a compound of formula (I)

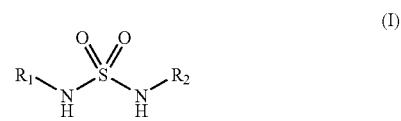

wherein $R_1$ and $R_2$ may be the same or different,
when $R_1$ and $R_2$ are different,
$R_1$ is selected from the group consisting of linear $C_{12}$-$C_{20}$ alkyl and linear $C_{12}$-$C_{20}$ alkenyl comprising 1, 2, 3 or 4 double bonds; and
$R_2$ is selected from the group consisting of hydrogen and $C_1$-$C_4$ alkyl;
or
when $R_1$ and $R_2$ are the same,
$R_1$ and $R_2$ are selected from the group consisting of linear $C_{14}$-$C_{20}$ alkyl and linear $C_{14}$-$C_{20}$ alkenyl with 1, 2, 3 or 4 double bonds;
and pharmaceutically acceptable salts, solvates and hydrates thereof;
for use as a medicament.

According to a third aspect, the present invention is directed to the use of an acyclic sulfamide derivative of formula (I)

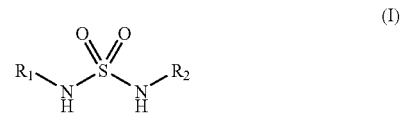

wherein $R_1$ and $R_2$ may be the same or different,
when $R_1$ and $R_2$ are different,
$R_1$ is selected from the group consisting of linear $C_{12}$-$C_{20}$ alkyl and linear $C_{12}$-$C_{20}$ alkenyl comprising 1, 2, 3 or 4 double bonds; and
$R_2$ is selected from the group consisting of hydrogen and $C_1$-$C_4$ alkyl;
or
when $R_1$ and $R_2$ are the same,
$R_1$ and $R_2$ are selected from the group consisting of linear $C_{14}$-$C_{20}$ alkyl and linear $C_{14}$-$C_{20}$ alkenyl with 1, 2, 3 or 4 double bonds;
and pharmaceutically acceptable salts, solvates and hydrates thereof;

for the manufacture of a medicament for satiety induction and ingestion control, corporal fat modulation and lipidic metabolism regulation and for the treatment or prevention of diabetes and cardiovascular diseases.

According to a preferred embodiment, said disease or condition is mediated by the alpha subtype of the peroxisome proliferator activated receptors.

As used in this description, a 'PPARalpha ligand' is a compound which binds to human PPARalpha and to co-activating molecules to provoke transcription processes just as described afterwards in the GST binding assay.

According to a preferred embodiment, said disease or condition is selected from the group consisting of diabetes and cardiovascular diseases.

According to a preferred embodiment, the compounds of formula (I) are useful for the manufacture of a medicament for satiety induction and ingestion control, corporal fat modulation or lipidic metabolism regulation.

According to a further preferred embodiment, the present invention refers to the use of the compounds of formula (I) and pharmaceutically acceptable salts, solvates and hydrates thereof, for the manufacture of a medicament for the prevention or treatment of obesity.

Although, obesity is a medical condition which can be in the origin of serious diseases, the skilled person will readily appreciate that the compounds of formula (I) can also be used for the reduction of weight due to aesthetic reasons.

According to a preferred embodiment, the compounds of formula (I) are used for the manufacture of a medicament for reducing a lipodystrophy.

For the purposes of the present invention, lipodystrophy is understood is a medical condition characterized by abnormal or degenerative conditions of the body's adipose tissue.

The invention also provides a method for satiety induction and ingestion control, corporal fat modulation and lipidic metabolism regulation and for the treatment or prevention of diabetes and cardiovascular diseases comprising administering to a patient in need of such treatment a therapeutically effective amount of a compound of formula (I)

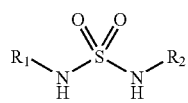

(I)

wherein $R_1$ and $R_2$ may be the same or different,
  when $R_1$ and $R_2$ are different,
    $R_1$ is selected from the group consisting of linear $C_{12}$-$C_{20}$ alkyl and linear $C_{12}$-$C_{20}$ alkenyl comprising 1, 2, 3 or 4 double bonds; and
    $R_2$ is selected from the group consisting of hydrogen and $C_1$-$C_4$ alkyl;
  or
  when $R_1$ and $R_2$ are the same,
    $R_1$ and $R_2$ are selected from the group consisting of linear $C_{14}$-$C_{20}$ alkyl and linear $C_{14}$-$C_{20}$ alkenyl with 1, 2, 3 or 4 double bonds;
and pharmaceutically acceptable salts, solvates and hydrates thereof.

According to a further aspect, the present invention is directed to a pharmaceutical composition which comprises:

a) a compound of formula (I)

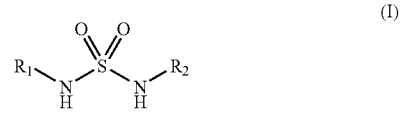

(I)

wherein $R_1$ and $R_2$ may be the same or different,
  when $R_1$ and $R_2$ are different,
    $R_1$ is selected from the group consisting of linear $C_{12}$-$C_{20}$ alkyl and linear $C_{12}$-$C_{20}$ alkenyl comprising 1, 2, 3 or 4 double bonds; and
    $R_2$ is selected from the group consisting of hydrogen and $C_1$-$C_4$ alkyl;
  or
  when $R_1$ and $R_2$ are the same,
    $R_1$ and $R_2$ are selected from the group consisting of linear $C_{14}$-$C_{20}$ alkyl and linear $C_{14}$-$C_{20}$ alkenyl with 1, 2, 3 or 4 double bonds; and
b) one or more pharmaceutically acceptable excipients.

The term "excipient" refers to a diluent, adjuvant, carrier, or vehicle with which the active ingredient is administered. Such pharmaceutical excipients can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The excipients and auxiliary substances necessary to manufacture the desired pharmaceutical form of administration of the pharmaceutical composition of the invention will depend, among other factors, on the elected administration pharmaceutical form. Said pharmaceutical forms of administration of the pharmaceutical composition will be manufactured according to conventional methods known by the skilled person in the art. A review of different active ingredient administration methods, excipients to be used and processes for producing them can be found in "Tratado de Farmacia Galénica", C. Faulí i Trillo, Luzán 5, S. A. de Ediciones, 1993.

The term "prevention or treatment" in the context of this specification means administration of a compound or composition according to the invention to preserve health in a patient suffering or in risk of suffering diabetes or a cardiovascular diseases. Said terms also include administration of a compound or composition according to the invention to prevent, ameliorate or eliminate one or more symptoms associated with diabetes or a cardiovascular disease.

For its administration to a subject, such as a mammal, e.g., a human, in need of treatment, the pharmaceutical composition of the invention may be administered by any appropriate route (via), such as, oral (e.g., oral, sublingual, etc.), parenteral (e.g., subcutaneous, intramuscular, intravenous, intramuscular, etc.), vaginal, rectal, nasal, topical, ophtalmic, etc.

The pharmaceutical composition of the invention may be administered in the form of different preparations. Non limiting examples are preparations for oral administration, i.e. tablets, capsules, syrups or suspensions.

Generally an effective administered amount of a compound used in the invention will depend on the relative efficacy of the compound chosen, the severity of the disorder being treated, or the age, weight or mode of administration.

However, active compounds will typically be administered once or more times a day, for example 1, 2, 3 or 4 times daily, with typical total daily doses in the range of from 0.1 to 500 mg/kg/day.

The compounds used in the present invention may also be administered with other drugs to provide a combination therapy. The other drugs may form part of the same composition, or be provided as a separate composition for administration at the same time or at different time.

Cosmetic Uses

The fat modulating properties of the compounds of formula (I) are useful for the cosmetic treatment of cosmetic conditions related to the undesired accumulation of fat.

Therefore, mentioned above, a fifth aspect of the present invention is directed to the cosmetic use of a compound of formula (I)

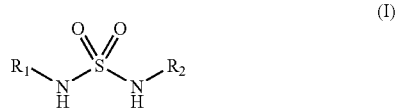

(I)

wherein $R_1$ and $R_2$ may be the same or different,
when $R_1$ and $R_2$ are different,
  $R_1$ is selected from the group consisting of linear $C_{12}$-$C_{20}$ alkyl and linear $C_{12}$-$C_{20}$ alkenyl comprising 1, 2, 3 or 4 double bonds; and
  $R_2$ is selected from the group consisting of hydrogen and $C_1$-$C_4$ alkyl;
or
when $R_1$ and $R_2$ are the same,
  $R_1$ and $R_2$ are selected from the group consisting of linear $C_{14}$-$C_{20}$ alkyl and linear $C_{14}$-$C_{20}$ alkenyl with 1, 2, 3 or 4 double bonds;
and pharmaceutically acceptable salts, solvates and hydrates thereof;
for reducing subcutaneous fat.

According to a preferred embodiment, the compound of formula (I) is used for reducing cellulite.

For the purposes of the present invention cellulite is understood as the dimpling of skin caused by the protrusion of subcutaneous fat into the dermis creating an undulating dermal-subcutaneous fat junction adipose tissue.

The compounds of this invention can be prepared through the usual organic chemistry just as illustrated by the enclosed operative examples. The following examples are displayed to illustrate the synthesis of some particular compounds of the present invention and to exemplify their biological properties. According to the preceding, the next examples section does not intend to limit in any way the scope of the invention defined in the present description.

EXAMPLES

In this description, the symbols and conventions used are consistent with those used in the International System and the contemporary scientific literature, for example the Journal of Medicinal Chemistry. Unless otherwise stated, the starting materials were obtained from commercial suppliers and were used without additional purification. Specifically, the following abbreviations may be used in the examples and throughout the whole description: g (grams); mg (milligram); kg (kilograms); µg (micrograms); l or L (liters); ml or mL (milliliters); µl or µL (microliters). mmol (milimols); mol (mols); mp (melting point); MS (Mass spectra); IP+ (Ionic Pulverization); Anal. (Elemental Analysis); TEA (triethylamine) MeOH (methanol); THF (tetrahydrofurane); EtOH (ethanol); CDCl3 (deuterated chloroform); DMSO (dimethylsulfoxide); GST (glutation sulfur-transferase); PBS (saline phosphate buffer); TIF2 (transcription intermediary factor 2). Unless indicated otherwise, all temperatures are given in ° C. (celsius).

Example 1

Preparation of N-(cis-9-octadecenyl)sulfamide (1), Also Known as N-oleylsulfamide To a stirred solution of 0.20 g of sulfamide (2.1 mmol) in 20 ml of $H_2O$ under reflux it is added dropwise 0.1 ml (2.1 mmol) of N-oleylamine in 10 ml of EtOH for 30 minutes. The reaction mixture is stirred and refluxed for 6 hours. Then the solvent is evaporated and the white solid is purified in a chromatography column, using $CH_2Cl_2$:MeOH/$NH_3$ 9.4:0.6 as eluent; 0.52 g of white solid are obtained. Yield 72%; mp=68-70 C;

$^1$H NMR (300 MHz, CDCl$_3$): 5.32 (m, 2H); 4.59 (br s, 2H); 4.38 (br s, 1H); 3.09 (q, J=7.0 Hz, 2H); 1.97 (m, 4H); 1.55 (m, 2H); 1.24 (m, 22H); 0.85 (t, J=6.7 Hz, 3H).

$^{13}$C NMR (75 MHz, CDCl3): 129.9; 129.7; 43.6; 31.8; 29.7-26.6; 27.1; 27.2; 22.6; 14.1.

MS (ES+) [M+H]+ 347 (100%). Anal. ($C_{18}H_{38}N_2SO_2$, 346.57): C, H, N, S.

Example 2

Preparation of N-octadecylsulfamide (2)

0.270 g, (1.0 mmol) of N-octadecylamine and 0.100 g (1.0 mmol) of sulfamide in 50 ml of THF (50 mL) are stirred and refluxed for 51 h. The solvent is evaporated and the crude is purified in a chromatography column, using $CH_2Cl_2$:MeOH/ $NH_3$ 9:1 as eluyent. 0.06 g of white solid are obtained. Yield 18%; mp=105-107° C.;

$^1$H NMR (400 MHz, DMSO-d6): 6.39 (br s, 2H); 6.33 (br s, 1H); 2.82 (m, 2H); 1.42 (m, 2H); 1.21 (bm, 30H); 0.83 (t, J=6.8 Hz, 3H).

$^{13}$C NMR (100 MHz, DMSO-d$_6$): 42.7; 31.4; 29.1; 26.5; 22.2; 14.1;

MS (ES+) [M+H]+ 349 (100%). Anal. ($C_{18}H_{40}N_2SO_2$, 348.64): C, H, N, S.

Example 3

Preparation of N-hexadecylsulfamide (3)

The title compound was prepared following the procedure previously described in Example 1, using 0.5 g (2.0 mmol) of N-hexadecylamine and 0.195 g (2.0 mmol) of sulfamide as starting reagent. 0.087 g of a white solid were obtained. Yield 16%; m.p. 102-104° C.

$^1$H-NMR (500 MHz, DMSO-d$_6$) δ: 2.83 (c, 2H, |J|=6.8 Hz $CH_2NHSO_2$); 1.43 (t, 2H, |J|=6.8 Hz, $CH_2$—$CH_2NHSO_2$); 1.23 (s, 20H, —$CH_2$—); 0.85 (t, 3H, J=6.8 Hz, $CH_2$—$CH_3$).

$^{13}$C-NMR (125 MHz, DMSO-d$_6$) δ: 42.5 ($CH_2$NH); 31.3 ($CH_2$—$CH_2$NH); 29.0-28.7 (—$CH_2$—); 26.4 ($CH_2$—$CH_2$—$CH_2$NH); 22.1 ($CH_2$—$CH_3$); 13.9 ($CH_2$—$CH_3$).

Anal (C$_{16}$H$_{36}$N$_2$SO$_2$) % theor. (% found): C, 59.95 (59.68); H, 11.32 (11.04); N, 8.74 (8.65); S, 10.00 (9.91).

Example 4

Preparation of N-tetradecylsulfamide (4)

The title compound was prepared following the procedure previously described in Example 1, using 0.43 g (2.0 mmol) of N-tetradecylamine and 0.2 g (2.0 mmol) of sulfamide as starting reagent. 0.37 g of a white solid were obtained. Yield 63%; m.p. 99-101° C.

$^1$H-NMR (300 MHz, DMSO-d$_6$) δ: 2.83 (c, 2H, |J|=6.7 Hz CH$_2$NHSO$_2$); 1.42 (t, 2H, |J|=6.7 Hz, CH$_2$—CH$_2$NHSO$_2$); 1.22 (s, 22H, —CH$_2$—); 0.83 (t, 3H, J=7.0 Hz, CH$_2$—CH$_3$).

$^{13}$C-NMR (75 MHz, DMSO-d$_6$) δ: 42.5 (CH$_2$NH); 31.4 (CH$_2$—CH$_2$NH); 29.0-28.7 (—CH$_2$—); 26.4 (CH$_2$—CH$_2$—CH$_2$NH); 22.1 (CH$_2$—CH$_3$); 13.9 (CH$_2$—CH$_3$).

Anal (C$_{14}$H$_{32}$N$_2$SO$_2$) % theor. (% found): C, 57.49 (57.25); H, 11.03 (10.97); N, 9.58 (9.47); S, 10.96 (11.21).

Example 5

Preparation of N-dodecylsulfamide (5)

The title compound was prepared following the procedure previously described in Example 1.

$^1$H-NMR (500 MHz, DMSO-d6) δ: 2.80 (c, 2H, |J|=6.8 Hz CH$_2$NHSO$_2$); 1.41 (t, 2H, |J|=6.7 Hz, CH$_2$—CH$_2$NHSO$_2$); 1.22 (s, 20H, —CH$_2$—); 0.83 (t, 3H, |J|=6.8 Hz, CH$_2$—CH$_3$).

$^{13}$C-NMR (125 MHz, DMSO-d6) δ: 42.6 (CH$_2$NH); 31.3 (CH$_2$—CH$_2$NH); 29.1-28.7 (—CH$_2$—); 26.4 (CH$_2$—CH$_2$—CH$_2$NH); 22.1 (CH$_2$—CH$_3$); 13.9 (CH$_2$—CH$_3$).

Anal (C$_{12}$H$_{28}$N$_2$SO$_2$) % theor. (% found): C, 54.51 (54.80); H, 10.67 (10.57); N, 10.59 (10.80); S, 12.13 (11.94).

Example 6

Preparation of N-(cis-9-octadecenyl)-N'-propylsulfamide, also Known as N-oleyl-N'-propylsulfamide (6)

0.20 g (1.2 mmol) of freshly distilled N-propylsulfamoyl chloride were added dropwise to a solution of the amine and TEA in dry toluene at 0° C. under nitrogen atmosphere. The reaction mixture was stirred at room temperature, and the white solid (TEA.HCl) was filtered, the solvent was evaporated to dryness and the crude was purified by column chromatography on silica gel with CH$_2$Cl$_2$:MeOH/NH$_3$ 9:1, providing the desired product (0.27 g) as a white solid. Yield 58%; m.p. 82-83° C.

$^1$H NMR (400 MHz, CDCl$_3$) δ: 5.30 (m, 2H, CH=CH); 4.25 (br s, 2H, NH); 2.97 (m, 4H, CH$_2$NHSO$_2$NHCH$_2$); 1.97 (m, 4H, CH$_2$CH=CHCH$_2$); 1.54 (sextet, 2H, J=7.3 Hz, CH$_2$—CH$_3$(Pr)); 1.51 (m, 2H, CH$_2$CH$_2$NHSO$_2$); 1.21 (bm, 22H, —CH$_2$—); 0.91 (t, 3H, J=7.3 Hz, CH$_2$—CH$_3$(Pr)); 0.84 (t, 3H, J=6.6 Hz, CH$_2$—CH$_3$ (oleyl)).

$^{13}$C NMR (100 MHz, CDCl$_3$) δ: 129.9, 129.7 (CH=CH); 44.9 (NHSO$_2$NHCH$_2$(Pr)); 43.2 (oleyl-CH$_2$NHSO$_2$); 31.8 (CH$_2$—CH$_2$CH$_3$); 29.8-28.9, 26.7 (—CH$_2$—); 27.1, (CH$_2$—CH=CH—CH$_2$); 22.8 (CH$_2$—CH$_3$(Pr)); 22.6 (CH$_2$—CH$_3$ (oleyl)); 14.1 (CH$_3$ (oleyl)); 11.2 (CH$_3$(Pr)).

Anal (C$_{21}$H$_{44}$N$_2$SO$_2$) % theor. (% found): C, 64.86 (65.06); H, 11.32 (11.60); N, 7.20 (7.34); S, 8.23 (8.33).

Example 7

Preparation of N-octadecyl-N'-propylsulfamide (7)

The title compound was prepared following the method described in Example 6. The starting reactants are 0.54 g (2.0 mmol) of N-octadecylamine and 0.31 g (2.0 mmol) of N-propylsulfamoyl chloride. 0.06 g of a white solid were obtained. Yield 31%; m.p. 110-112° C.

$^1$H NMR (400 MHz, CDCl$_3$): 3.01 (m, 4H); 1.53 (m, 4H); 1.24 (bm, 30H); 0.94 (t, J=7.6 Hz, 3H); 0.86 (t, J=6.8 Hz, 3H)

$^{13}$C NMR (100 MHz, CDCl$_3$): 45.0; 43.3; 31.9; 29.7-29.2, 26.7; 22.9; 22.6; 14.1; 11.2;

MS (ES+) [M+H]+ 391 (100%). Anal. (C$_{21}$H$_{46}$N$_2$SO$_2$, 390.67): C, H, N, S.

Example 8

Preparation and Obtaining of N-hexadecyl-N'-propylsulfamide (8)

The title compound was prepared following the method described in Example 6. The starting reactants are 0.15 g (0.6 mmol) of N-hexadecylamine and 0.10 g (0.6 mmol) of N-propylsulfamoyl chloride. 0.15 g of a white solid were obtained. Yield 70%; m.p. 108-110° C.

$^1$H NMR (300 MHz, CDCl$_3$) δ: 4.06 (bm, 2H, NH); 3.0 (m, 4H, CH$_2$NHSO$_2$); 1.55 (m, 4H, CH$_2$CH$_2$NHSO$_2$); 1.23 (bm, 26H, —CH$_2$—); 0.93 (t, 3H, J=7.3 Hz, CH$_3$(Pr)); 0.86 (t, 3H, |J|=6.6 Hz, CH$_3$ (hexadecyl)).

$^{13}$C NMR (75 MHz, CDCl$_3$) δ: 44.9 (CH$_2$NH(Pr)); 43.2 (CH$_2$NHSO$_2$ (hexadecyl)); 31.9 (CH$_2$CH$_2$CH$_3$); 29.7-29.2, 26.7 (—CH$_2$—); 22.9 (CH$_2$—CH$_3$(Pr)); 22.6 (CH$_2$CH$_3$ (hexadecyl); 14.1 (CH$_3$ (hexadecyl)); 11.2 (CH$_2$—CH$_3$(Pr)).

Anal (C$_{19}$H$_{42}$N$_2$SO$_2$) % theor. (% found): C, 62.93 (62.71); H, 11.67 (11.90); N, 7.73 (7.49); S, 8.84 (9.12).

Example 9

Preparation of N-propyl-N'-tetradecylsulfamide (9)

The title compound was prepared following the method described Example 6. The starting reactants are 0.10 g (0.5 mmol) of N-tetradecylamine and 0.076 g (0.5 mmol) of N-propylsulfamoyl chloride. 0.092 g of a white solid are obtained. Yield 55%; m.p. 105-107° C.

$^1$H NMR (300 MHz, CDCl$_3$) δ: 4.08 (bm, 2H, NH); 3.0 (m, 4H, CH$_2$NHSO$_2$); 1.55 (m, 4H, CH$_2$CH$_2$NHSO$_2$); 1.23 (bm, 22H, —CH$_2$—); 0.93 (t, 3H, J=7.3 Hz, CH$_3$(Pr)); 0.85 (t, 3H, |J|=6.4 Hz, CH$_3$ (tetradecyl)).

$^{13}$C NMR (75 MHz, CDCl$_3$) δ: 44.9 (CH$_2$NH(Pr)); 43.2 (CH$_2$NHSO$_2$ (tetradecyl)); 31.9 (CH$_2$CH$_2$CH$_3$); 29.6-29.2, 26.7 (—CH$_2$—); 22.9 (CH$_2$—CH$_3$(Pr)); 22.7 (CH$_2$CH$_3$ (tetradecyl); 14.1 (CH$_3$ (tetradecyl)); 11.2 (CH$_2$—CH$_3$(Pr)).

Anal (C$_{17}$H$_{38}$N$_2$SO$_2$) % theor. (% found): C, 61.03 (60.87); H, 11.45 (11.68); N, 8.37 (8.09); S, 9.58 (9.86).

Example 10

Preparation of N-(1-adamantyl)-N'-propylsulfamide (10)

The title compound was prepared following the method described in Example 6.

$^1$H NMR (400 MHz, CDCl$_3$) δ: 4.05 (br s, 2H, NH); 3.02 (t, 2H, J=7.1 Hz, CH$_2$NHSO$_2$); 2.10 (m, 3H, H-3 (adamantyl)); 1.94 (m, 6H, H-2 (adamantyl)); 1.66 (m, 6H, H-4 (adamantyl)); 1.60 (sextet, 2H, J=7.3 Hz, J=7.1 Hz, CH$_2$CH$_3$(Pr)); 0.96 (t, 3H, J=7.3 Hz, CH$_3$(Pr)).

$^{13}$C NMR (100 MHz, CDCl$_3$) δ: 54.3 (C-1 (adamantyl)); 45.2 (CH$_2$NHSO$_2$ (Pr)); 42.7 (C-2 (adamantyl)); 35.9 (C-4 (adamantyl)); 29.4 (C-3 (adamantyl)); 22.7 (CH$_2$—CH$_3$ (Pr)); 11.3 (CH$_2$—CH$_3$(Pr)).

Anal (C₁₃H₂₄N₂SO₂) % theor. (% found): C, 57.32 (57.11); H, 8.88 (8.70); N, 10.28 (9.98); S, 11.77 (11.85).

Example 11

Preparation of N-(1-adamantyl)-N'-Propylsulfamide (11)

The title compound was prepared following the method described in Example 6.

¹H NMR (400 MHz, CDCl₃) δ: 4.18 (m, 1H, NH); 4.04 (d, 1H, |J|=9.6 Hz, NH); 3.02 (c, 2H, |J|=7.1 Hz, CH₂NHSO₂); 2.94 (dc, 1H, |J|$_{CH3}$=6.8 Hz, |J|$_{NH}$=9.6 Hz, H(1)); 2.00 (ma, 3H, H(3)); 1.68 (d, 3H, J=12.0 Hz, H(4ec)); 1.59 (d, 6H, |J|=12.0 Hz, H(2)ec y H(4)ax); 1.57 (sextet, 2H, J=7.3 Hz, CH₂—CH₃(Pr)); 1.42 (d, 3H, |J|=12.0 Hz, H(2)ax); 1.17 (d, 3H, |J|=6.7 Hz, CH₃ (adamantyl)); 0.95 (t, 3H, |J|=7.3 Hz, CH₂—CH₃(Pr)).

¹³C NMR (100 MHz, CDCl₃) δ: 58.7 (C(1) (adamantyl)); 45.0 (NHCH₂SO₂); 38.3 (C(4) (adamantyl)); 36.9 (C(2) (adamantyl)); 28.2 (C(3) (adamantyl)); 22.9 (CH₂—CH₃(Pr)); 11.3 (CH₂—CH₃(Pr)); 15.4 (CH₃ (adamantyl)).

Anal (C₁₅H₂₈N₂SO₂) % theor. (% found): C, 60.00 (60.18); H, 9.33 (9.61); N, 9.33 (9.36); S, 10.66 (10.91).

Example 12

Preparation of N-propyl-N'-adamantylsulfamide (12)

The title compound was prepared following the procedure previously described in Example 6.

¹H NMR (400 MHz, CDCl₃) δ: 4.82 (d, 1H. |J|=7.6 Hz, NH (adamantyl)); 4.47 (t, 1H, |J|=6.1 Hz, NH(Pr)); 3.48 (d, 1H, |J|=7.6 Hz, H(2) (adamantyl)); 2.99 (c, 2H, |J|=6.1 Hz, |J|=7.1 Hz, CH₂NHSO₂); 1.94 (ma, 2H, H(1) y H(3) (adamantyl)); 1.83 (m, 2H, H(4)ax y H(10)ax(adamantyl)); 1.81 (m, 2H, H(5) y H(7) (adamantyl)); 1.85-1.74 (m, 6H, H(8) y H(9)(adamantyl)); 1.69 (2H, m, H(6)); 1.58 (m, 2H, H(4)ec y H(10)ec (adamantyl)); 1.57 (sextet, 2H, |J|=7.3 Hz, |J|=7.1 Hz, CH₂—CH₃(Pr)); 0.94 (t, 3H, |J|=7.3 Hz, CH₂—CH₃ (Pr)).

¹³C NMR (100 MHz, CDCl3) δ: 57.7 (C(2) (adamantyl)); 44.9 (CH₂NHSO₂); 37.3 (C(6), C(8) and C(9) (adamantyl)); 32.8 (C(3) y C(1) (adamantyl)); 31.3 (C(4) y C(10) (adamantyl)); 26.9 (C(5) y C(7) (adamantyl)); 22.8 (CH₂—CH₃(Pr)); 11.2 (CH₂—CH₃(Pr)).

Anal (C₁₃H₂₄N₂SO₂) % theor. (% found): C, 57.32 (57.60); H, 8.88 (9.02); N, 10.28 (10.44); S, 11.77 (12.01).

Example 13

Preparation of N,N'-bis(9-cis-octadecenyl)sulfamide, Also Known as N,N-dioleylsulfamide (13)

0.68 ml of N-oleylamine (1.4 mmol) are added dropwise to 0.20 g of N-propylsulfamide (1.4 mmol) in 2 ml of water at room temperature. The colourless mixture reaction is stirred under reflux for 48 h, showing an orange colour. The solvent is evaporated and the crude is purified in a chromatography column, using CH₂Cl₂ as eluyent. 0.12 g of white solid (compound 1) and 0.26 g of white solid (compound 13) were obtained. Yield (compound 13): 22%; m.p. 85-88° C.

¹H-NMR (400 MHz, CDCl₃) δ: 5.32 (m, 4H, CH=CH); 4.25 (bs, 2H, NH); 3.00 (m, 8H, CH₂NHSO₂); 1.99 (m, 8H, CH₂—CH=CH—CH₂); 1.53 (sextet, J=7.3 Hz, 4H, CH₂CH₃); 1.26 (bm, 44H); 0.87 (t, 3H, J=7.3 Hz, CH₃).

¹³C-NMR (100 MHz, CDCl₃) δ: 129.9, 129.7 (CH=CH); 43.2 (CH₂NHSO₂); 31.9 (CH₂—CH₂CH₃); 29.7, 29.6, 29.5, 29.4, 29.3, 29.2, 27.2, 26.7 (—CH₂); 22.6 (CH₂—CH₃); 14.0 (CH₃)

Example 14

Preparation of N-(cis-9-cis-12-octadecadienyl)sulfamide (14)

The title compound was prepared following the procedure described previously in Example 1, using 0.044 g (0.16 mmol) of N-(cis-9-cis-12-octadecadienyl)amine and 0.016 g (0.16 mmol) of sulfamide. 0.007 g of white solid were obtained. Yield 12%; m.p. 55-57° C.

¹H-NMR (400 MHz, CDCl₃) δ: 5.33 (m, 4H, CH=CH); 4.59 (bs, 2H, NH₂); 4.36 (bs, 1H, NH); 3.10 (m, 2H, CH₂NHSO₂); 2.76 (m, 2H, C=CH—CH₂—CH=C); 2.03 (m, 4H, CH=CH—CH₂CH₂); 1.56 (m, 2H, CH₂—CH₂NHSO₂); 1.29 (m, 16H, —CH₂—); 0.87 (t, 3H, |J|=7.0 Hz, CH₂—CH₃).

¹³C-NMR (100 MHz, CDCl₃) δ: 130.2, 130.0, 128.1, 127.9 (CH=CH); 43.6 (CH₂NH); 31.5 (CH₂—CH₂CH₃); 29.1 (CH₂—CH₂NHSO₂); 27.2 (CH=CH—CH₂CH₂); 29.6-26.6 (—CH₂—); 25.6 (C=CH—CH₂—CH=C); 22.5 (CH₂—CH₃); 14.0 (CH₂—CH₃).

Example 15

Preparation of N-(cis-5-cis-8-cis-11-cis-14-eicosatetraenyl)sulfamide (15)

The title compound was prepared following the procedure described previously in Example 1, using 0.10 g (0.3 mmol) of N-(cis-5-cis-8-cis-11-cis-14-eicosatetraenyl)amine and 0.03 g (0.3 mmol) of sulfamide. Yield 14%; m.p. oil.

¹H-NMR (400 MHz, CDCl₃) δ: 5.37 (m, 8H, CH=CH); 4.60 (bs, 2H, NH₂); 4.37 (bs, 1H, NH); 3.13 (m, 2H, CH₂NHSO₂); 2.81 (m, 6H, C=CH—CH₂—CH=C); 2.07 (m, 4H, CH=CH—CH₂CH₂); 1.60 (m, 2H, CH₂—CH₂NHSO₂); 1.43 (m, 2H, CH₂—CH₂CH₂NHSO₂); 1.30 (m, 6H, —CH₂—); 0.89 (t, 3H, |J|=6.8 Hz, CH₂—CH₃).

¹³C-NMR (100 MHz, CDCl₃) δ: 130.7, 129.4, 128.6, 128.5, 128.2, 128.0, 127.8, 127.7 (CH=CH); 43.7 (CH₂NH); 31.8 (CH₂—CH₂CH₃); 29.8, 29.3 (CH₂—CH₂CH₂CH₃, CH₂—CH₂NHSO₂); 27.4 (CH=CH—CH₂CH₂); 26.8 (CH₂—CH₂CH₂NHSO₂); 25.6 (C=CH—CH₂—CH=C); 22.8 (CH₂—CH₃); 14.3 (CH₂—CH₃).

Example 16

Preparation of N-(cis-5-cis-8-cis-11-cis-14-eicosatetraenyl)-N'-propylsulfamide (16)

The title compound was prepared following the method described in Example 6. The starting reactants are 0.35 g (1.2 mmol) of N-(cis-5-cis-8-cis-11-cis-14-eicosatetraenyl) amine and 0.19 g (1.2 mmol) of N-propylsulfamoyl chloride. 0.09 g of yellow oil are obtained. Yield 18%; m.p. oil.

¹H-NMR (400 MHz, CDCl₃) δ: 5.34 (m, 8H, CH=CH); 4.25 (bs, 1H, NH ((Pr)); 4.22 (bs, 1H, NH (araquidonyl)); 3.02 (m, 2H, CH₂NHSO₂); 2.81 (m, 6H, C=CH—CH₂—CH=C); 2.07 (m, 4H, CH=CH—CH₂CH₂); 1.54 (m, 2H, CH₂NHSO₂); 1.57 (sextet, 2H, |J|=7.3 Hz, CH₂CH₃ (Pr)); 1.42 (m, 2H, CH₂—CH₂CH₂NHSO₂); 1.29 (ma, 6H, —CH₂—); 0.95 (t, 3H, |J|=7.3 Hz, CH₃(Pr)); 0.89 (t, 3H, |J|=7.0 Hz, CH₃ (araquidonyl)).

$^{13}$C-NMR (100 MHz, CDCl$_3$) δ: 130.5, 129.4, 128.6, 128.5, 128.3, 128.1, 127.8, 127.5 (CH=CH); 44.9 (CH$_2$NH (Pr)); 43.1 (CH$_2$NHSO$_2$ (araquidonyl)); 31.5 (CH$_2$—CH$_2$CH$_3$); 27.1 (CH=CH—CH$_2$CH$_2$); 29.3 (CH$_2$—CH$_2$CH$_2$CH$_3$); 26.8 (CH$_2$—CH$_2$CH$_2$NH SO$_2$); 25.6 (C=CH—CH$_2$—CH=C); 22.8 (CH$_2$—CH$_3$(Pr)); 22.5 (CH$_2$—CH$_3$ (araquidonyl)); 14.3 (CH$_2$—CH$_3$ (araquidonyl)); 11.2 (CH$_2$—CH$_3$(Pr)).

Example 17

Preparation of N-(cis-9-cis-12-octadecadienyl)N'-propylsulfamide (17)

The title compound was prepared following the method described in Example 6. The starting reactants are 0.09 g (0.35 mmol) of N-(cis-9-cis-12-octadecadienyl)amine and 0.05 g (0.35 mmol) of N-propylsulfamoyl chloride. 0.02 g of a white solid are obtained. Yield 17%; m.p. 70-75° C.

$^1$H-NMR (400 MHz, CDCl$_3$) δ: 5.34 (m, 4H, CH=CH); 4.27 (sa, 1H, NH, (Pr)); 4.25 (bs, 1H, NH (linoleyl)); 3.01 (m, 4H, CH$_2$NHSO$_2$); 2.77 (m, 2H, C=CH—CH$_2$—CH=C); 2.05 (m, 4H, CH=CH—CH$_2$CH$_2$); 1.60 (m, 4H, CH$_2$—CH$_2$NH); 1.29 (m, 16H, —CH$_2$—); 0.95 (t, 3H, |J|=7.3 Hz, CH$_3$(Pr)); 0.87 (t, 3H, |J|=6.7 Hz, CH$_3$ (linoleyl)).

$^{13}$C-NMR (100 MHz, CDCl$_3$) δ: 130.2, 130.0, 128.0, 127.9 (CH=CH); 44.9 (SO$_2$NHCH$_2$ (Pr)); 43.2 (linoleyl-CH$_2$NH); 31.5 (CH$_2$—CH$_2$CH$_3$)) 29.1 (CH$_2$—CH$_2$NHSO$_2$); 27.2 (CH=CH—CH$_2$CH$_2$); 29.6-26.6 (—CH$_2$—); 25.6 (C=CH—CH$_2$—CH=C); 22.8 (CH$_2$—CH$_3$(Pr)); 22.5 (CH$_2$—CH$_3$ (linoleyl)); 14.0 (CH$_3$ (linoleyl)); 11.2 (CH$_3$ (Pr)).

Example 18

Preparation of N-trans-9-octadecenylamine, Also Known as N-elaidylamine

To a stirred solution of trans-9-octadecanoic acid (1 mol) in Et$_2$O, a suspension of LiAlH$_4$ (6 mol) in Et$_2$O was added dropwise at 10° C. under nitrogen atmosphere. Stirring continued at 10° C. for 30 minutes, and then the mixture was refluxed for 30 minutes, after which the reaction mixture was allowed to cool to room temperature. A mixture of ice and H$_2$SO$_4$ was added carefully. The organic phase was separated and extracted with Et$_2$O and the combined organic phases were washed with a NaHCO$_3$ solution and a saturated NaCl solution, and dried with MgSO$_4$. The mixture was filtered over celite and the solvent evaporated to obtain trans-9-octadecan-1-ol.

This alcohol was dissolved in pyridine and mesyl chloride was added (1.5 mol) at 0° C. under nitrogen atmosphere. The mixture was stirred for 4 hours and then poured over cold water and extracted with ethyl acetate. The organic phases were washed with H$_2$SO$_4$ 1N and with a saturated solution of NaHCO$_3$, dried over MgSO$_4$, and the solvent evaporated.

The mesylate derivative obtained was dissolved in anhydrous DMF, and NaN$_3$ (5 mol) was added at room temperature. The reaction mixture was heated for 21 hours, then allowed to cool to room temperature and filtered. The filtrate was washed with 100 ml of cold water. The mixture was extracted with ethyl acetate and dried over MgSO$_4$, and the solvent was evaporated. The crude product was purified by chromatographic column using hexane:ethyl acetate (6:1) as eluent.

The resulting azide was dissolved in Et$_2$O and LiAlH$_4$ (3 mol) in Et$_2$O was added dropwise at room temperature. The reaction mixture was refluxed for 4 hours, and then Et$_2$O with traces of water was added. The suspension was filtered, acidified with HCl 6M, and then basified with NaOH 10% in the presence of Et$_2$O. The combined organic phases were dried over MgSO$_4$, the solvent evaporated and the product purified by chromatographic column using CH$_2$Cl$_2$:MeOH/NH$_3$ (9:1). Yield 44%; m.p. 28-30° C.

$^1$H-NMR (400 MHz, CDCl$_3$) δ: 5.37 (m, 2H, H(9) y H(10)); 2.94 (m, 2H, H(1)); 1.95 (m, 4H, H(8) y H(11)); 1.72 (m, 2H, H(2)); 1.26 (m, 22H, —CH$_2$—); 0.88 (t, 3H, J=6.4 Hz, CH$_2$—CH$_3$).

$^{13}$C-NMR (100 MHz, CDCl$_3$) δ: 130.5, 130.1 (C(9) y C(10)); 40.1 (C(1)); 32.6 y 32.5 (C(8) y C(11)); 31.8 (C(16)); 29.7, 29.6, 29.5, 29.4, 29.3, 29.2, 29.1, 29.0, 28.9 (—CH$_2$—); 26.5 (C(3)); 22.7 (CH$_2$—CH$_3$); 14.1 (CH$_2$—CH$_3$).

EM (ES+): [M+H]$^+$ 268 (100%); (C$_{20}$H$_{37}$N, 267.49).

Example 19

Preparation of N-(trans-9-octadecenyl)sulfamide (19)

The title compound was prepared following the procedure previously described in Example 1, using 0.112 g (1.1 mmol) of N-trans-9-octadecenylamine and 0.312 g (1.1 mmol) of sulfamide as starting reagent. 0.240 g of a white solid were obtained. Yield 63%; m.p. 88-90° C.

$^1$H-NMR (400 MHz, CDCl$_3$) δ: 5.39 (m, 2H, H(9) y H(10)); 4.53 (ma, 2H, NH$_2$); 4.29 (ma, 1H, NH); 3.14 (m, 2H, H(1)); 2.03 (m, 4H, H(8) y H(11)); 1.53 (m, 2H, H(2)); 1.28 (m, 22H, —CH$_2$—); 0.88 (t, 3H, |J|=6.4 Hz, CH$_2$—CH$_3$).

$^{13}$C-NMR (100 MHz, CDCl$_3$) δ: 130.5, 130.2 (C(9) y C(10)); 43.6 (C(1)); 32.6 y 32.5 (C(8) y C(11)); 31.8 (C(16)); 29.6, 29.5, 29.4, 29.3, 29.2, 29.1, 29.0 (—CH$_2$—); 26.6 (C(3)); 22.7 (CH$_2$—CH$_3$); 14.1 (CH$_2$—CH$_3$).

EM (ES+): [M+H]$^+$ 347 (100%). Anal. Calculated (C$_{18}$H$_{38}$N$_2$SO$_2$, 346.57): C, 62.38; H, 11.05; N, 8.08; S, 9.25. Found C, 62.38; H, 11.35; N, 8.18; S, 8.95.

Example 20

Preparation of N-(trans-9-octadecenyl)-N'-Propylsulfamide (20)

The title compound was prepared following the method described Example 6. The starting reactants are 0.102 g (0.38 mmol) of N-trans-9-octadecenylamine and 0.021 g (0.38 mmol) of N-propylsulfamoyl chloride and 0.078 ml of TEA (0.57 mmol). 0.07 g of a white solid are obtained. Yield 48%; m.p. 91-93° C.

$^1$H-NMR (400 MHz, CDCl$_3$) δ: 5.38 (m, 2H, H(9) y H(10)); 4.06 (bm, 2H, NH); 3.00 (m, 2H, H(1) y H(1')); 1.95 (m, 4H, H(8) y H(11)); 1.58 (sextet, 2H, H(2')); 1.55 (m, 2H, H(2)); 1.26 (m, 22H, —CH$_2$—); 0.95 (t, 3H, |J|=7.3 Hz, CH$_2$—CH$_3$(Pr)); 0.87 (t, 3H, J=6.4 Hz, CH$_2$—CH$_3$).

$^{13}$C-NMR (100 MHz, CDCl$_3$) δ: 130.5, 130.2 (C(9) y C(10)); 44.9 (C(1')); 43.2 (C(1)); 32.6 y 32.5 (C(8) y C(11)); 31.9 (C(16)); 29.7, 29.6, 29.5, 29.4, 29.3, 29.2, 29.1, 29.0 (—CH$_2$—); 26.7 (C(3)); 22.9 (CH$_2$—CH$_3$(Pr)); 22.7 (CH$_2$—CH$_3$); 14.1 (CH$_2$—CH$_3$); 11.2 (CH$_3$(Pr)).

EM (ES+): [M+H]$^+$ 389 (100%). Anal. Calculated (C$_{21}$H$_{44}$N$_2$SO$_2$, 388.65): C, 64.86; H, 11.32; N, 7.20; S, 8.23. Found C, 64.58; H, 11.61; N, 7.50; S, 8.35.

Biological Assays
In Vitro Interaction Assay of PPARalpha Protein with TIF2 and GST Fusion Protein (GST-Pull-Down Assays).

The precipitation through GST (also known as GST-pull down) is an in vitro method used to determine and assess the existence of physical interactions between proteins, being useful in our case to confirm the ligand induced interaction of the PPAR-α transcription factor and the TIF2 co-activator (Macias-Gonzalez, M et al. *J. Biol. Chem.* 277 (2002): 18501). From the 4B sepharose-glutation resins with GST alone or GST-TIF2$_{646-926}$ at 50% in PBS, a centrifugation was carried out to eliminate the supernatant, and a blocking buffer was added to the precipitated phase to avoid unspecific binding with PBS and bovine serum albumin (Aldrich), centrifugating again. Afterwards, immune precipitation buffer (at 50%) was added to the precipitated phase. 50 μL were taken from the sepharose-glutation resin with GST or GST-TIF2 in immune precipitation buffer and then added: 20 μL of PPAR-α labelled with $^{35}$[S] pre-incubated with the possible ligand, 8 μL of the same ligand in 100% DMSO and 22 μL of immune precipitation buffer for 20 minutes at 30° C. and 40 minutes at room temperature. After the incubation, the labelled proteins which did not result in a fusion with GST-TIF2$_{646-926}$ bound to sepharose through glutation were washed with the immune precipitation buffer after were centrifuged at maximum speed.

Once the supernatant was removed, the precipitated phase with the labelled complexes bound to sepharose was resuspended with the protein loader buffer (in a proportion 1:1 in volume) and was stirred at about 95° C. for 5 minutes, separating the sepharose resin from the GST-TIF2$_{646-926}$ complex with $^{35}$[S] PPAR-α after a new centrifugation of 5 minutes at maximum speed. Then, the different samples of the supernatant were loaded in the gel and a SDS-PAGE electrophoresis was carried out at 100 V for an hour approximately. Finally, the gels were quantified and visualized with a phosphorescence Fuji FLA3000 reader using a Fuji Image Gauge software.

As shown in FIG. 1, the compounds of the invention show PPARalpha activity.

Cellular Transfection and Luciferase Reporter Gene Assay (RGA)

Breast cancer human cells MCF-7 were seeded in a 6-well culture plate (105 cells/mL) and cultured in a Dulbecco modified Eagle medium (DMEM) free from phenol red, supplied with 5% of fetal bovine serum (FBS) treated with carbon (Macias-Gonzalez, M et al. *Mol. End.* 17 (2003): 2028).

The liposomes with DNA plasmids were obtained by incubation of 1 μg of the reporter plasmid with luciferase and the wild type human PPAR-α expression vector with 10 μg of N-1-(2,3-dioleyloxi)-propyl-N,N,N-trimethylammonium (DOTAP from Roche Diagnostics) for 15 minutes at room temperature in a total volume of 100 μL. After the dilution with 900 μL of DMEM free from phenol red, the liposomes were added to the cells. 4-5 h after the transfection of the cells, the DMEM free from phenol red supplemented with 500 μL of FBS treated with carbon at 15% was added, in this case with the PPAR-α ligands (OEA, AEA and sulfamides derivatives) or control solvents (DMSO) at different concentrations of $10^{-8}$, $10^{-7}$, $10^{-6}$ and $10^{-5}$ M.

The cells were lysed 16 hours after the beginning of the stimulation with the reporter gene lysis buffer (Roche Diagnostics) and the reporter gene assay or RGA luciferase of constant luminous signal was carried out following the manufactures recommendations (Roche Diagnostics). The luciferase activities were standardized with regard to the protein concentration and the induction factors were calculated as the ratio of luciferase activity of ligand stimulated cells in relation to the solvent controls (Vaisanen, S. et al. *Mol. Pharmacol.* 62 (2002):788).

Figure 2:
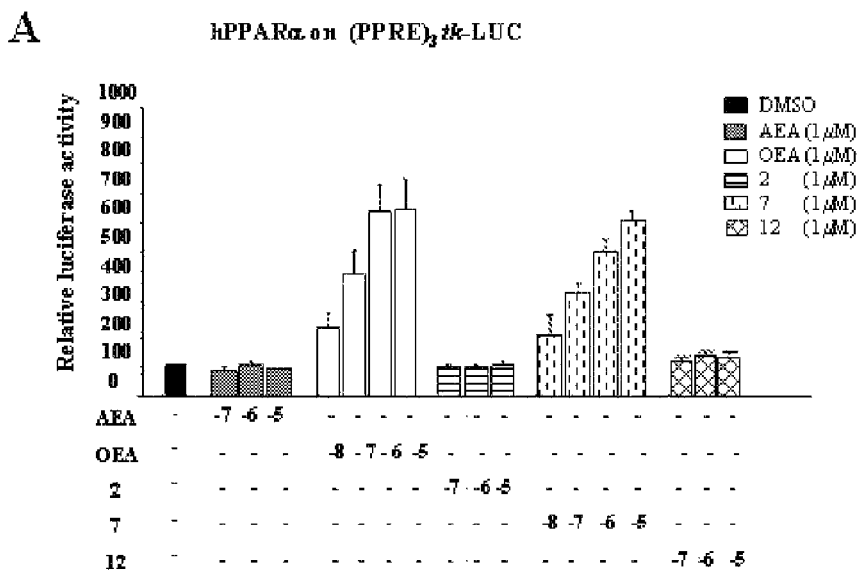
FIG. 2: Agonistic action of OEA and analogs. Luciferase reporter gene assays were performed with extracts from MCF-7 cells that were transiently transfected with a luciferase reporter construct containing three copies of the human ACO of PPRE. (A) Wild type human PPARα expression vector was also cotransfected as indicated. Cells were treated for 16 h with solvent (DMSO), and different concentrations (*$10^{-8}$, *$10^{-7}$, $10^{-6}$ and $10^{-5}$ M) of OEA, compound 2, or *$10^{-7}$, $10^{-6}$ and $10^{-5}$ M of anandamide (AEA, used as a negative control), 7 (*$10^{-8}$, *$10^{-7}$, $10^{-6}$ and $10^{-5}$ M) and 12 (*$10^{-7}$, $10^{-6}$ and $10^{-5}$ M). (*p<0.05, (**) p<0.01 vs vehicle, #p<0.01 vs vehicle and without ACO) (B) Wild type human PPARα expression as well as plasmids coding full length TIF2 were also cotransfected as indicated. Cells were treated for 16 h with solvent (DMSO), 10 μM WY14643, 1 μM OEA and its analogs 2, 7 and 12. Relative luciferase activities were measured in reference to solvent-induced cells not overexpressing any protein. Columns represent the mean of at least three experiments and bars indicate SD. (*p<0.01 vs vehicle, #p<0.01 vs vehicle and without TIF2).
Figure 2:
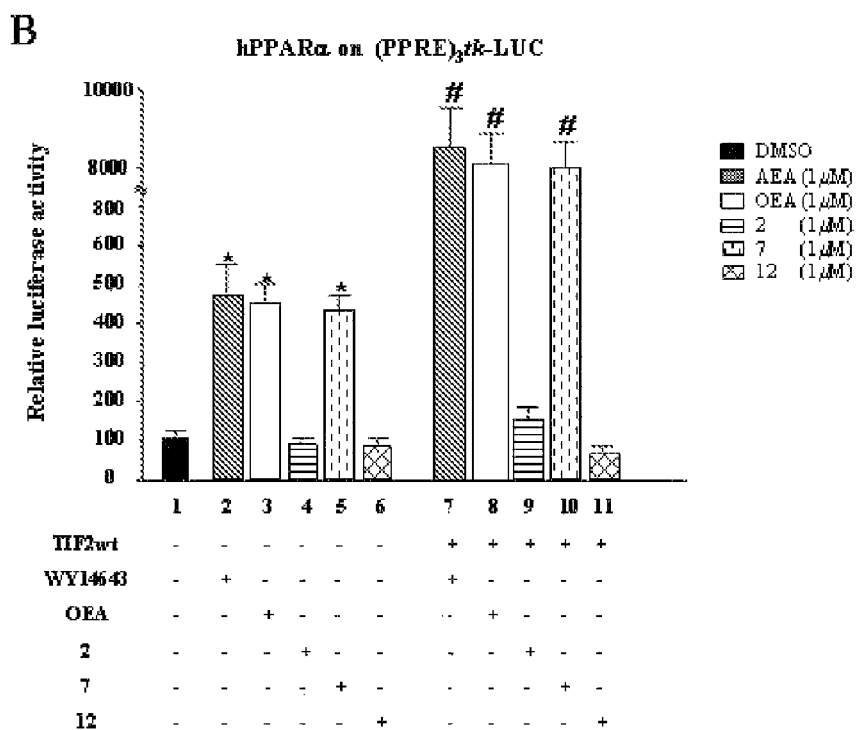

The incorporation of the propyl substitution gives more transcriptional activity at the PPARR (FIG. 2A).

WY14643 was included as positive control because this hypolipidemic fibrate selectively activates PPARR. At endogenous coregulator levels, the basal level of PPARR on the PPRE (lane 1) was induced nearly 6 times higher by OEA, WY14643, and compound 7 (lanes 2, 3, and 5), whereas the application of compounds 2 and 12 did not provide induction (lanes 4 and 6). The overexpression of TIF2 resulted in a significant increase in the basal level (lane 1) and a subsequently high prominent increase of agonist-stimulated values (lane 7, 8, and 10). However, the application of compounds 2 and 12 did not provide significantly higher induction (lanes 9 and 11). disorders.

Food Intake Study: Acute Treatment

The effects of the different compounds on feeding behaviour were analyzed in male Wistar rats deprived of food for 24 hours, which were accustomed to its manipulation (Navarro, M et al. 1996 *J. Neurochem.* 67 (1996):1982. Rodriguez de Fonseca, F. et al. *Nature* 414 (2001):209. Fu, J et al. *Nature,* 425 (2003):90). For this aim, 48 hours before every assay rats were set out in single cages, the base material (sand or sawdust) was removed and little food containers were set out into the cage for 4 hours. After this initial phase, animals were deprived of food for 24 hours, always with free access to water. After 24 hours of fast, different treatment groups were established (N=8-10 every group) and different doses of the sulfamide corresponding to each experimental session were administrated i.p. in their vehicle solution in a volume of 1 mL/kg, as well as a control group only treated with the vehicle:

1) Group treated with a 0.03 mg/kg dose of the sulfamide in vehicle solution.
2) Group treated with a 3 mg/kg dose of the sulfamide in vehicle.
3) Group with a 3 mg/kg dose of the corresponding sulfamide in vehicle.
4) Control group treated with the vehicle tween-80 at 5% in physiological serum.

15 minutes after the administration, the containers with a known food amount (normally 30-40 g) and a bottle of fresh water were placed. These containers were weighted 30, 60, 120 and 240 minutes after their presentation, so that the food ingested by each animal was controlled.

Figure 3:
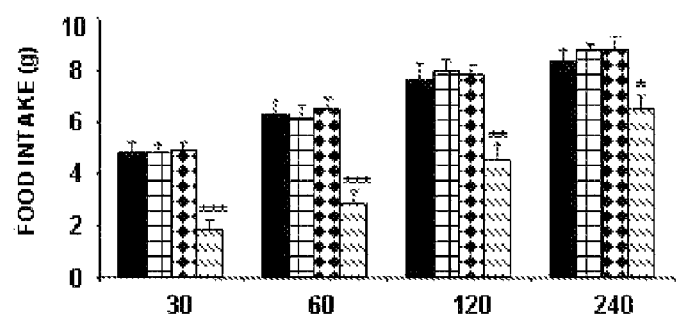
FIG. 3: Activity of OEA analogs as feeding suppressants. Food intake in food-deprived animals was tested 30, 60, 120 and 240 min after the i.p injection of the different compounds synthesized at different doses. Here we show results for compounds 2 (A), 7 (B), 12 (C), 19 (D) and 20 (E). 2 is a compound that does not activate PPARα but reduces feeding behaviour; 7 is a potent feeding suppressant and a potent activator of PPARα, and, finally, 12 neither activates PPARα nor suppress food intake. Results are means±SEM of at least three determinations per group. (*) p<0.05, () p<0.01, (*) p<0.001, versus vehicle, ANOVA.
Figure 3:
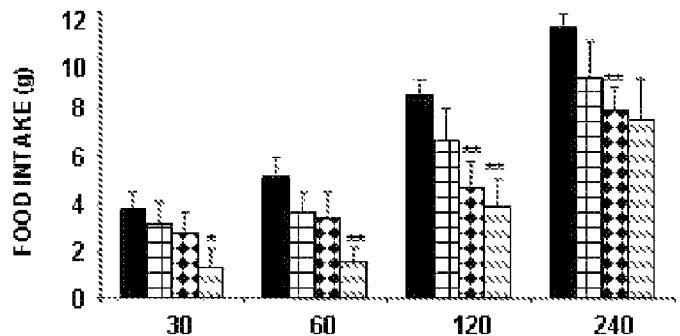
Figure 3:
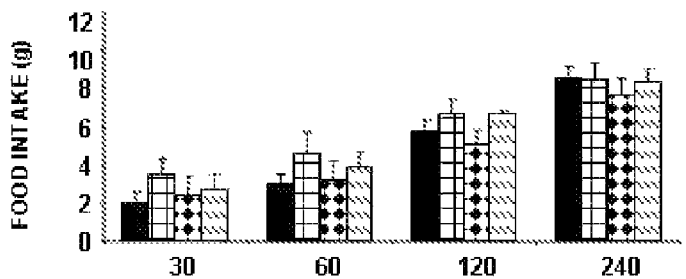
Figure 3:
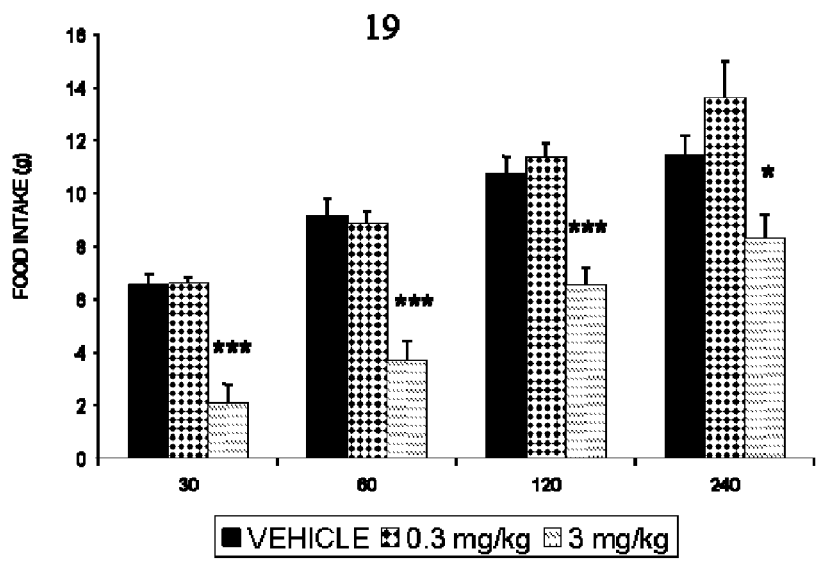
Figure 3:
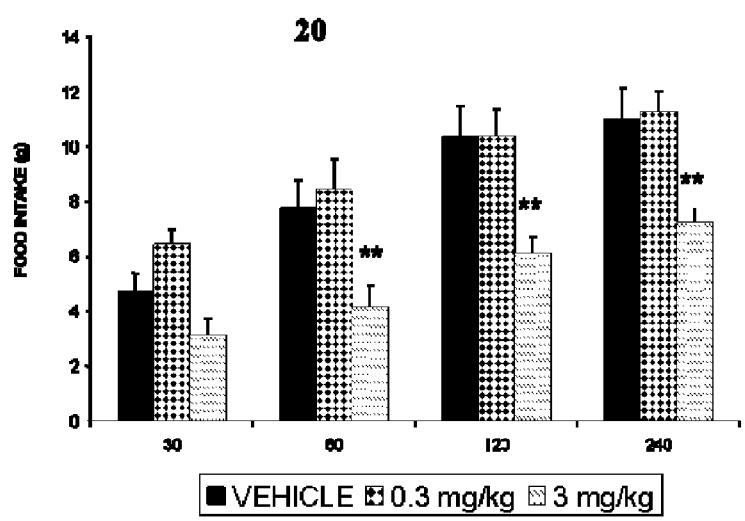

Results are shown in FIG. 3. An extended dose-response curve was done using i.p. injections in food-deprived animals. The fact that these sulfamoyl derivatives showed no cannabimetic properties and did not affect fatty acid amidohydrolase activity (data not shown) made them suitable candidates to study their effects on food intake and to compare them with those of OEA. This naturally occurring lipid has been found to decrease food intake through activation of the nuclear receptor PPARR. However, this was not always true. As an example, compound N-octadecylsulfamide (2) clearly reduced food intake but did not activate PPAR receptor-mediated transcription.

Food Intake Studies: Chronic Treatment

A chronic treatment with the compounds was carried out using male Wistar rats which were accustomed to its manipulation.

For this aim, rats were set out in single cages keeping the base material (sand or sawdust). After an adaptation phase to the conditions of the husbandry where the assay was carried out, three different groups (N=8 every group) were established according to the received treatment:
1) Group treated with example 6 in its vehicle solution with a 1 mg/kg dose.
2) Group treated with tween-80 vehicle at 5% in physiological serum.
3) Control group treated with physiological serum.

The total duration of the experiment was eight days, with two i.p. daily administrations (injected volume of 1 mL/kg) of the different solutions with an interval of 12 hours between both injections. Everyday and previously to the administration at 8:00, each animal was weighted. During the total time of the assay, the single weight of each animal and the biochemical parameters in serum were daily controlled.

Figure 4:
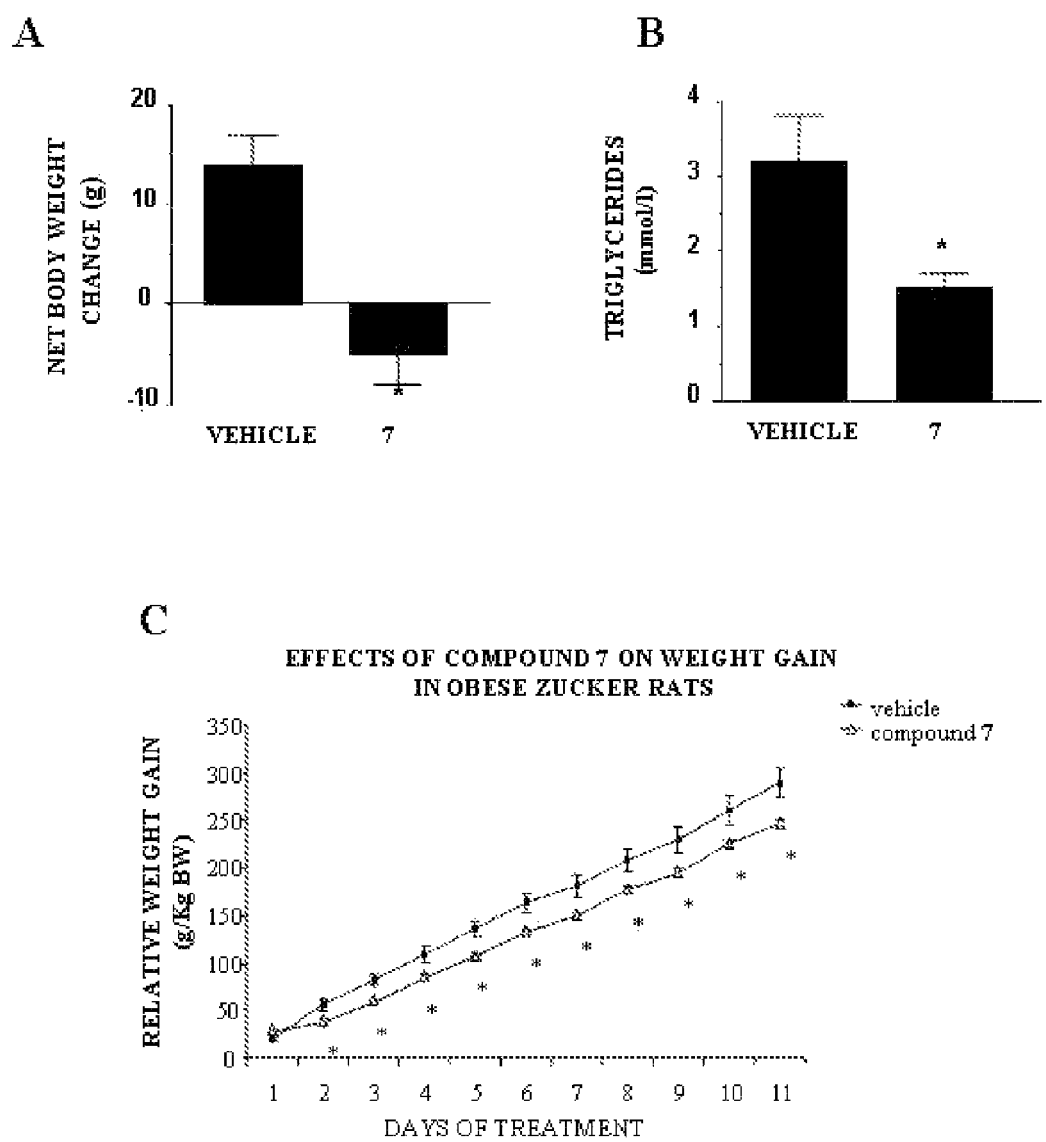
FIG. 4: Effects of chronic treatment with 7 (N-octadecyl-N'-propylsulfamide) on body weight gain and plasma triglycerides. Chronic treatment (8 days, 1 mg/kg, i.p. daily) with N-octadecyl-N'-propylsulfamide reduces body weight (A) and plasma triglyceride contents (B) when compared to vehicle-treated normal rats. Subchronic (11 days) administration of the compound 7 (1 mg/kg, i.p.) reduces cumulative relative weight gain (C) (g/kg of body weight at day 1) in obese Zucker rats. Results are means±SEM of at least three determinations per group. (*) p<0.05, versus vehicle, ANOVA.

Results are shown in FIG. 4. As expected for a PPAR receptor agonist, N-octadecyl-N'-propylsulfamide (7), reduced body weight (FIG. 4A) after 8 days of treatment and produced a marked reduction in plasma triglycerides (FIG. 4B). To further explore the anti-obesity properties of this compound, we used an additional animal model of obesity. Similar effects were observed in genetically obese Zucker (falfa) rats, and the daily administration of compound 7 (1 mg/kg, i.p.) for 11 days reduced body weight gain (FIG. 4C) and food intake. The potency of this new compound is greater than that of the natural ligand of PPARR, because it has been described that OEA hypolipemiant effects are present only at doses greater than 5 mg/kg, whereas N-octadecyl-N'-propylsulfamide (7) was found to be active at lower doses (1 mg/kg).

The invention claimed is:
1. Acyclic sulfamide derivatives of formula (I),

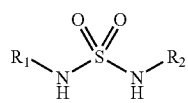

(I)

wherein $R_1$ and $R_2$ may be the same or different,
when $R_1$ and $R_2$ are different,
$R_1$ is selected from the group consisting of linear $C_{12}$-$C_{20}$ alkyl, and $R_2$ is selected from the group consisting of $C_1$-$C_4$ alkyl; or
$R_1$ is selected from the group consisting of linear $C_{12}$-$C_{20}$ alkenyl comprising 1, 2, 3 or 4 double bonds, and $R_2$ is selected from the group consisting of hydrogen and $C_1$-$C_4$ alkyl;
or
when $R_1$ and $R_2$ are the same,
$R_1$ and $R_2$ are selected from the group consisting of linear $C_{14}$-$C_{20}$ alkenyl with 1, 2, 3 or 4 double bonds;
and pharmaceutically acceptable salts thereof.

2. Acyclic sulfamide derivatives according to claim 1, wherein is a $C_1$-$C_4$ alkyl when $R_1$ and $R_2$ are different.

3. Acyclic sulfamide derivatives according to claim 2, wherein $R_2$ is propyl, when $R_1$ and $R_2$ are different.

4. Acyclic sulfamide derivatives according to claim 1, wherein $R_2$ is hydrogen, when $R_1$ and $R_2$ are different, and $R_1$ is selected from the group consisting of $C_{12}$-$C_{20}$ alkenyl comprising 1, 2, 3 or 4 double bonds.

5. Acyclic sulfamide derivatives according claim 1, wherein $R_1$ is a linear $C_{16}$-$C_{20}$ alkyl or a linear $C_{16}$-$C_{20}$ alkenyl comprising 1, 2, 3 or 4 double bonds, when $R_1$, and $R_2$ are different.

6. Acyclic sulfamide derivatives according to claim 5, wherein the alkenyl group of $R_1$ has 1 double bond when $R_1$ and $R_2$ are different.

7. Acyclic sulfamide derivatives according to claim 1, with chemical name:
N-(cis-9-octadecenyl)sulfamide;
N-(cis-9-octadecenyl)-N'-propylsulfamide;
N-octadecyl-N'-propylsulfamide;
N-hexadecyl-N'-propylsulfamide;
N-propyl-N'-tetradecylsulfamide;
N,N'-bis(9-cis-octadecenyl)sulfamide;
N-(cis-9-cis-12-octadecadienyl)sulfamide;
N-(cis-5-cis-8-cis-11-cis-14-eicosatetraenyl)sulfamide;
N-(cis-5-cis-8-cis-11-cis-14-eicosatetraenyl)-N'-propylsulfamide;
N-(cis-9-cis-12-octadecadienyl)-N'-propylsulfamide;
N-(trans-9-octadecenyl)sulfamide; and
N-(trans-9-octadecenyl)-N-propylsulfamide;
and pharmaceutically acceptable salts thereof.

8. A pharmaceutical composition which comprises:
a) a compound of formula (I)

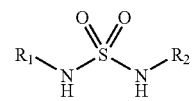

(I)

wherein $R_1$ and $R_2$ may be the same or different,
when $R_1$ and $R_2$ are different,
$R_1$ is selected from the group consisting of linear $C_{12}$-$C_{20}$ alkyl and linear $C_{12}$-$C_{20}$ alkenyl comprising 1, 2, 3 or 4 double bonds; and
$R_2$ is selected from the group consisting of hydrogen and $C_1$-$C_4$ alkyl;
or
when $R_1$ and $R_2$ are the same,
$R_1$ and $R_2$ are selected from the group consisting of linear $C_{14}$-$C_{20}$ alkyl and linear $C_{14}$-$C_{20}$ alkenyl with 1, 2, 3 or 4 double bonds; and
b) one or more pharmaceutically acceptable excipients.

9. A method for satiety induction and ingestion control, corporal fat modulation and lipidic metabolism regulation and for the treatment or prevention of diabetes and cardiovascular diseases comprising administering to a patient in need of such treatment a therapeutically effective amount of a compound of formula (I)

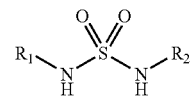

(I)

wherein $R_1$ and $R_2$ may be the same or different,
when $R_1$, and $R_2$, are different,
$R_1$ is selected from the group consisting of linear $C_{12}$-$C_{20}$ alkyl and linear $C_{12}$-$C_{20}$ alkenyl comprising 1, 2, 3 or 4 double bonds; and
$R_2$ is selected from the group consisting of hydrogen and $C_1$-$C_4$ alkyl;
or
when $R_1$ and $R_2$ are the same,
$R_1$ and $R_2$ are selected from the group consisting of linear $C_{14}$-$C_{20}$ alkyl and linear $C_{14}$-$C_{20}$ alkenyl with 1, 2, 3 or 4 double bonds;
and pharmaceutically acceptable salts thereof.

10. The method according to claim 9, wherein the method is for the treatment or prevention of diabetes and cardiovascular diseases.

11. The method according to claim 9, wherein the method is for satiety induction and ingestion control, corporal fat modulation and lipidic metabolism regulation.

12. The method according to claim 9, wherein the method is for the prevention or treatment of obesity.

13. The method according to claim 9, wherein the method is for reducing a lipodystrophy.

14. A method for satiety induction and ingestion control, corporal fat modulation and lipidic metabolism regulation and for the treatment or prevention of diabetes and cardiovascular diseases comprising administering to a patient in need of such treatment a therapeutically effective amount of a compound selected from the group consisting of:
N-(cis-9-octadecenyl)sulfamide;
N-octadecylsulfamide;
N-hexadecylsulfamide;
N-tetradecylsulfamide;
N-(cis-9-octadecenyl)-N'-propylsulfamide;
N-octadecyl-N'-propylsulfamide;
N-hexadecyl-N'-propylsulfamide;
N-propyl-N'-tetradecylsulfamide;
N,N'-bis(9-cis-octadecenyl)sulfamide;
N-(cis-9-cis-12-octadecadienyl)sulfamide;
N-(cis-5-cis-8-cis-11-cis-14-eicosatetraenyl)sulfamide;
N-(cis-5-cis-8-cis-11-cis-14-eicosatetraenyl)-N'-propylsulfamide;
N-(cis-9-cis-12-octadecadienyl)-N'-propylsulfamide;
N-(trans-9-octadecenyl)sulfamide; and
N-(trans-9-octadecenyl)-N'-propylsulfamide;
and pharmaceutically acceptable salts thereof.

15. The method according to claim 14, wherein the method is for the treatment or prevention of diabetes and cardiovascular diseases.

16. The method according to claim 14, wherein the method is for satiety induction and ingestion control, corporal fat modulation and lipidic metabolism regulation.

17. The method according to claim 14, wherein the method is for the prevention or treatment of obesity.

18. The method according to claim 14, wherein the method is for reducing a lipodystrophy.

19. A cosmetic method for reducing subcutaneous fat comprising administering to a patient a compound of formula (I)

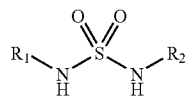

(I)

wherein $R_1$ and $R_2$ may be the same or different,
when $R_1$ and $R_2$ are different,
$R_1$ is selected from the group consisting of linear $C_{12}$-$C_{20}$ alkyl and linear $C_1$,—$C_{12}$-$C_{12\text{-}20}$ alkenyl comprising 1, 2, 3 or 4 double bonds; and
$R_2$ is selected from the group consisting of hydrogen and $C_1$-$C_4$ alkyl;
or
when $R_1$ and $R_2$ are the same,
$R_1$ and $R_2$ are selected from the group consisting of linear $C_{14}$-$C_{20}$ alkyl and linear $C_{14}$-$C_{20}$ alkenyl with 1, 2, 3 or 4 double bonds;
and pharmaceutically acceptable salts thereof.

20. The method according to claim 19, wherein the said method is for reducing cellulite.

21. A cosmetic method for reducing subcutaneous fat comprising administering to a patient a compound selected from the group consisting of:
N-(cis-9-octadecenyl)sulfamide;
N-octadecylsulfamide;
N-hexadecylsulfamide;
N-tetradecylsulfamide;
N-(cis-9-octadecenyl)-N'-propylsulfamide;
N-octadecyl-N'-propylsulfamide;
N-hexadecyl-N'-propylsulfamide;
N-propyl-N'-tetradecylsulfamide;
N,N'-bis(9-cis-octadecenyl)sulfamide;
N-(cis-9-cis-12-octadecadienyl)sulfamide;
N-(cis-5-cis-8-cis-11-cis-14-eicosatetraenyl)sulfamide;
N-(cis-5-cis-8-cis-11-cis-14-eicosatetraenyl)-N'-propylsulfamide;
N-(cis-9-cis-12-octadecadienyl)-N'-propylsulfamide;
N-(trans-9-octadecenyl)sulfamide; and
N-(trans-9-octadecenyl)-N'-propyl sulfamide;
and pharmaceutically acceptable salts thereof.

22. The method according to claim 21, wherein the said method is for reducing cellulite.

23. A pharmaceutical composition which comprises:
a) a compound selected from the group consisting of:
N-(cis-9-octadecenyl)sulfamide;
N-octadecylsulfamide;
N-hexadecylsulfamide;
N-tetradecylsulfamide;
N-(cis-9-octadecenyl)-N'-propylsulfamide;
N-octadecyl-N'-propylsulfamide;
N-hexadecyl-N"-propylsulfamide;
N-propyl-N"-tetradecylsulfamide;
N,N'-bis(9-cis-octadecenyl)sulfamide;
N-(cis-9-cis-12-octadecadienyl)sulfamide;
N-(cis-5-cis-8-cis-11-cis-14-eicosatetraenyl)sulfamide;
N-(cis-5-cis-8-cis-11-cis-14-eicosatetraenyl)-N'-propylsulfamide;
N-(cis-9-cis-12-octadecadienyl)-N'-propylsulfamide;
N-(trans-9-octadecenyl)sulfamide; and
N-(trans-9-octadecenyl)-N-propylsulfamide; and
b) one or more pharmaceutically acceptable excipients.

* * * * *